United States Patent [19]
Davis et al.

[11] Patent Number: 5,814,464
[45] Date of Patent: Sep. 29, 1998

[54] NUCLEIC ACIDS ENCODING TIE-2 LIGAND-2

[76] Inventors: Samuel Davis, 332 W. 88th St., Apt. B. 2, New York, N.Y. 10024; Pamela F. Jones, 85 Karen St., Fairfield, Conn. 06430; George D. Yancopoulos, 1519 Baptist Church Rd., Yorktown Heights, N.Y. 10598

[21] Appl. No.: 418,595

[22] Filed: Apr. 6, 1995

Related U.S. Application Data

[63] Continuation-in-part of Ser. No. 373,579, Jan. 17, 1995, which is a continuation-in-part of Ser. No. 353,503, Dec. 9, 1994, which is a continuation-in-part of Ser. No. 348,492, Dec. 2, 1994, which is a continuation-in-part of Ser. No. 330,261, Oct. 27, 1994, Pat. No. 5,521,073, which is a continuation-in-part of Ser. No. 319,932, Oct. 7, 1994.

[51] Int. Cl.$^6$ .......................... C12N 15/12; C07K 14/435
[52] U.S. Cl. .................... 435/69.5; 435/70.1; 435/240.2; 435/252.3; 435/320.1; 935/22; 935/69; 935/70; 935/72; 536/23.1; 536/23.5
[58] Field of Search .................. 435/69.5, 70.1, 435/240.2, 172.3, 252.3, 320.1; 536/23.1, 23.5; 935/11, 22, 66, 69, 70, 72

[56] References Cited

PUBLICATIONS

Partanen et al. (1990) Proc. Natl. Acad. Sci. vol. 87, pp. 8913–8917.
Partanen et al. (1992) Mol. & Cell. Biology, vol. 12, No. 4, pp. 1698–1707.

*Primary Examiner*—John Ulm
*Assistant Examiner*—Prema Mertz

[57] ABSTRACT

The present invention provides for an isolated nucleic acid molecule encoding a human TIE-2 ligand. In addition, the invention provides for a receptor body which specifically binds a human TIE-2 ligand. The invention also provides an antibody which specifically binds a human TIE-2 ligand. The invention further provides for an antagonist of human TIE-2. The invention also provides for therapeutic compositions as well as a method of blocking blood vessel growth, a method of promoting neovascularization, a method of promoting the growth or differentiation of a cell expressing the TIE-2 receptor, a method of blocking the growth or differentiation of a cell expressing the TIE-2 receptor and a method of attenuating or preventing tumor growth in a human.

11 Claims, 10 Drawing Sheets

Fig. 4A

```
              10         20         30         40         50         60         70         80
              .          .          .          .          .          .          .          .
   CAGCTGACTCAGGCAGGCTCCATGCTGAACGGTCACACAGAGAGGAAACAATAAATCTCAGCTACTATGCAATAAATATC 90        100        110        120        130        140        150        160
              .          .          .          .          .          .          .          .
   TCAAGTTTTAACGAAGAAAAACATCATTGCAGTGAAATAAAAAATTTTAAAATTTTAGAACAAAGCTAACAAATGGCTAG 170        180        190        200        210        220        230        240
              .          .          .          .          .          .          .          .
   TTTTCTATGATTCTTCTTCAAACGCTTTCTTTGAGGGGGAAAGAGTCAAACAAACAAGCAGTTTTACCTGAAATAAAGAA 250        260        270        280        290        300        310
              .          .          .          .          .          .          .
   CTAGTTTTAGAGGTCAGAAGAAAGGAGCAAGTTTTGCGAGAGGCACGGAAGGAGTGTGCTGGCAGTACA ATG ACA
                                                                           M   T>

320        330        340        350        360        370
              .          .          .          .          .          .
   GTT TTC CTT TCC TTT GCT TTC CTC GCT GCC ATT CTG ACT CAC ATA GGG TGC AGC AAT CAG
    V   F   L   S   F   A   F   L   A   A   I   L   T   H   I   G   C   S   N   Q>

380        390        400        410        420        430
              .          .          .          .          .          .
   CGC CGA AGT CCA GAA AAC AGT GGG AGA AGA TAT AAC CGG ATT CAA CAT GGG CAA TGT GCC
    R   R   S   P   E   N   S   G   R   R   Y   N   R   I   Q   H   G   Q   C   A>

440        450        460        470        480        490
              .          .          .          .          .          .
   TAC ACT TTC ATT CTT CCA GAA CAC GAT GGC AAC TGT CGT GAG AGT ACG ACA GAC CAG TAC
    Y   T   F   I   L   P   E   H   D   G   N   C   R   E   S   T   T   D   Q   Y>

500        510        520        530        540        550
              .          .          .          .          .          .
   AAC ACA AAC GCT CTG CAG AGA GAT GCT CCA CAC GTG GAA CCG GAT TTC TCT TCC CAG AAA
    N   T   N   A   L   Q   R   D   A   P   H   V   E   P   D   F   S   S   Q   K>

560        570        580        590        600        610
              .          .          .          .          .          .
   CTT CAA CAT CTG GAA CAT GTG ATG GAA AAT TAT ACT CAG TGG CTG CAA AAA CTT GAG AAT
    L   Q   H   L   E   H   V   M   E   N   Y   T   Q   W   L   Q   K   L   E   N>

620        630        640        650        660        670
              .          .          .          .          .          .
   TAC ATT GTG GAA AAC ATG AAG TCG GAG ATG GCC CAG ATA CAG CAG AAT GCA GTT CAG AAC
    Y   I   V   E   N   M   K   S   E   M   A   Q   I   Q   Q   N   A   V   Q   N>

680        690        700        710        720        730
              .          .          .          .          .          .
   CAC ACG GCT ACC ATG CTG GAG ATA GGA ACC AGC CTC CTC TCT CAG ACT GCA GAG CAG ACC
    H   T   A   T   M   L   E   I   G   T   S   L   L   S   Q   T   A   E   Q   T>

740        750        760        770        780        790
              .          .          .          .          .          .
   AGA AAG CTG ACA GAT GTT GAG ACC CAG GTA CTA AAT CAA ACT TCT CGA CTT GAG ATA CAG
    R   K   L   T   D   V   E   T   Q   V   L   N   Q   T   S   R   L   E   I   Q>

800        810        820        830        840        850
              .          .          .          .          .          .
   CTG CTG GAG AAT TCA TTA TCC ACC TAC AAG CTA GAG AAG CAA CTT CTT CAA CAG ACA AAT
    L   L   E   N   S   L   S   T   Y   K   L   E   K   Q   L   L   Q   Q   T   N>

860        870        880        890        900        910
              .          .          .          .          .          .
   GAA ATC TTG AAG ATC CAT GAA AAA AAC AGT TTA TTA GAA CAT AAA ATC TTA GAA ATG GAA
    E   I   L   K   I   H   E   K   N   S   L   L   E   H   K   I   L   E   M   E>

920        930        940        950        960        970
              .          .          .          .          .          .
   GGA AAA CAC AAG GAA GAG TTG GAC ACC TTA AAG GAA GAG AAA GAG AAC CTT CAA GGC TTG
    G   K   H   K   E   E   L   D   T   L   K   E   E   K   E   N   L   Q   G   L>

980        990       1000       1010       1020       1030
              .          .          .          .          .          .
   GTT ACT CGT CAA ACA TAT ATA ATC CAG GAG CTG GAA AAG CAA TTA AAC AGA GCT ACC ACC
    V   T   R   Q   T   Y   I   I   Q   E   L   E   K   Q   L   N   R   A   T   T>

1040       1050       1060       1070       1080       1090
              .          .          .          .          .          .
   AAC AAC AGT GTC CTT CAG AAG CAG CAA CTG GAG CTG ATG GAC ACA GTC CAC AAC CTT GTC
    N   N   S   V   L   Q   K   Q   Q   L   E   L   M   D   T   V   H   N   L   V>
```

Fig. 4B

```
      1100        1110        1120        1130        1140        1150
        .           .           .           .           .           .
AAT CTT TGC ACT AAA GAA GGT GTT TTA CTA AAG GGA GGA AAA AGA GAG GAA GAG AAA CCA
 N   L   C   T   K   E   G   V   L   L   K   G   G   K   R   E   E   E   K   P>

1160        1170        1180        1190        1200        1210
        .           .           .           .           .           .
TTT AGA GAC TGT GCA GAT GTA TAT CAA GCT GGT TTT AAT AAA AGT GGA ATC TAC ACT ATT
 F   R   D   C   A   D   V   Y   Q   A   G   F   N   K   S   G   I   Y   T   I>

1220        1230        1240        1250        1260        1270
        .           .           .           .           .           .
TAT ATT AAT AAT ATG CCA GAA CCC AAA AAG GTG TTT TGC AAT ATG GAT GTC AAT GGG GGA
 Y   I   N   N   M   P   E   P   K   K   V   F   C   N   M   D   V   N   G   G>

1280        1290        1300        1310        1320        1330
        .           .           .           .           .           .
GGT TGG ACT GTA ATA CAA CAT CGT GAA GAT GGA AGT CTA GAT TTC CAA AGA GGC TGG AAG
 G   W   T   V   I   Q   H   R   E   D   G   S   L   D   F   Q   R   G   W   K>

1340        1350        1360        1370        1380        1390
        .           .           .           .           .           .
GAA TAT AAA ATG GGT TTT GGA AAT CCC TCC GGT GAA TAT TGG CTG GGG AAT GAG TTT ATT
 E   Y   K   M   G   F   G   N   P   S   G   E   Y   W   L   G   N   E   F   I>

1400        1410        1420        1430        1440        1450
        .           .           .           .           .           .
TTT GCC ATT ACC AGT CAG AGG CAG TAC ATG CTA AGA ATT GAG TTA ATG GAC TGG GAA GGG
 F   A   I   T   S   Q   R   Q   Y   M   L   R   I   E   L   M   D   W   E   G>

1460        1470        1480        1490        1500        1510
        .           .           .           .           .           .
AAC CGA GCC TAT TCA CAG TAT GAC AGA TTC CAC ATA GGA AAT GAA AAG CAA AAC TAT AGG
 N   R   A   Y   S   Q   Y   D   R   F   H   I   G   N   E   K   Q   N   Y   R>

1520        1530        1540        1550        1560        1570
        .           .           .           .           .           .
TTG TAT TTA AAA GGT CAC ACT GGG ACA GCA GGA AAA CAG AGC AGC CTG ATC TTA CAC GGT
 L   Y   L   K   G   H   T   G   T   A   G   K   Q   S   S   L   I   L   H   G>

1580        1590        1600        1610        1620        1630
        .           .           .           .           .           .
GCT GAT TTC AGC ACT AAA GAT GCT GAT AAT GAC AAC TGT ATG TGC AAA TGT GCC CTC ATG
 A   D   F   S   T   K   D   A   D   N   D   N   C   M   C   K   C   A   L   M>

1640        1650        1660        1670        1680        1690
        .           .           .           .           .           .
TTA ACA GGA GGA TGG TGG TTT GAT GCT TGT GGC CCC TCC AAT CTA AAT GGA ATG TTC TAT
 L   T   G   G   W   W   F   D   A   C   G   P   S   N   L   N   G   M   F   Y>

1700        1710        1720        1730        1740        1750
        .           .           .           .           .           .
ACT GCG GGA CAA AAC CAT GGA AAA CTG AAT GGG ATA AAG TGG CAC TAC TTC AAA GGG CCC
 T   A   G   Q   N   H   G   K   L   N   G   I   K   W   H   Y   F   K   G   P>

1760        1770        1780        1790        1800        1810
        .           .           .           .           .           .
AGT TAC TCC TTA CGT TCC ACA ACT ATG ATG ATT CGA CCT TTA GAT TTT TGA AAG CGCAATGT
 S   Y   S   L   R   S   T   T   M   M   I   R   P   L   D   F   *

1820        1830        1840        1850        1860        1870        1880        1890
  .           .           .           .           .           .           .           .
CAGAAGCGATTATGAAAGCAACAAAGAAATCCGGAGAAGCTGCCAGGTGAGAAACTGTTTGAAAACTTCAGAAGCAAACA 1900        1910        1920        1930        1940        1950        1960        1970
  .           .           .           .           .           .           .           .
ATATTGTCTCCCTTCCAGCAATAAGTGGTAGTTATGTGAAGTCACCAAGGTTCTTGACCGTGAATCTGGAGCCGTTTGAG 1980        1990        2000        2010        2020        2030        2040        2050
  .           .           .           .           .           .           .           .
TTCACAAGAGTCTCTACTTGGGGTGACAGTGCTCACGTGGCTCGACTATAGAAAACTCCACTGACTGTCGGGCTTTAAAA 2060        2070        2080        2090        2100        2110        2120        2130
  .           .           .           .           .           .           .           .
AGGGAAGAAACTGCTGAGCTTGCTGTGCTTCAAACTACTACTGGACCTTATTTTGGAACTATGGTAGCCAGATGATAAAT

2140
  .
ATGGTAATTTC
```

Fig. 5A

```
          10          20          30          40          50          60          70          80
           •           •           •           •           •           •           •           •
CAGCTGACTCAGGCAGGCTCCATGCTGAACGGTCACACAGAGAGGAAACAATAAATCTCAGCTACTATGCAATAAATATC 90         100         110         120         130         140         150         160
           •           •           •           •           •           •           •           •
TCAAGTTTTAACGAAGAAAAACATCATTGCAGTGAAATAAAAAATTTTAAAATTTTAGAACAAAGCTAACAAATGGCTAG 170         180         190         200         210         220         230         240
           •           •           •           •           •           •           •           •
TTTTCTATGATTCTTCTTCAAACGCTTTCTTTGAGGGGGAAAGAGTCAAACAAACAAGCAGTTTTACCTGAAATAAAGAA 250         260         270         280         290         300         310
           •           •           •           •           •           •           •
CTAGTTTTAGAGGTCAGAAGAAAGGAGCAAGTTTTGCGAGAGGCACGGAAGGAGTGTGCTGGCAGTACA ATG ACA
                                                                       M   T>

320              330              340              350              360              370
     •                •                •                •                •                •
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q>

380              390              400              410              420              430
     •                •                •                •                •                •
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A>

440              450              460              470              480              490
     •                •                •                •                •                •
TAC ACT TTC ATT CTT CCA GAA CAC GAT GGC AAC TGT CGT GAG AGT ACG ACA GAC CAG TAC
 Y   T   F   I   L   P   E   H   D   G   N   C   R   E   S   T   T   D   Q   Y>

500              510              520              530              540              550
     •                •                •                •                •                •
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K>

560              570              580              590              600              610
     •                •                •                •                •                •
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N>

620              630              640              650              660              670
     •                •                •                •                •                •
TAC ATT GTG GAA AAC ATG AAG TCG GAG ATG GCC CAG ATA CAG CAG AAT GCA GTT CAG AAC
 Y   I   V   E   N   M   K   S   E   M   A   Q   I   Q   Q   N   A   V   Q   N>

680              690              700              710              720              730
     •                •                •                •                •                •
CAC ACG GCT ACC ATG CTG GAG ATA GGA ACC AGC CTC CTC TCT CAG ACT GCA GAG CAG ACC
 H   T   A   T   M   L   E   I   G   T   S   L   L   S   Q   T   A   E   Q   T>

740              750              760              770              780              790
     •                •                •                •                •                •
AGA AAG CTG ACA GAT GTT GAG ACC CAG GTA CTA AAT CAA ACT TCT CGA CTT GAG ATA CAG
 R   K   L   T   D   V   E   T   Q   V   L   N   Q   T   S   R   L   E   I   Q>

800              810              820              830              840              850
     •                •                •                •                •                •
CTG CTG GAG AAT TCA TTA TCC ACC TAC AAG CTA GAG AAG CAA CTT CTT CAA CAG ACA AAT
 L   L   E   N   S   L   S   T   Y   K   L   E   K   Q   L   L   Q   Q   T   N>

860              870              880              890              900              910
     •                •                •                •                •                •
GAA ATC TTG AAG ATC CAT GAA AAA AAC AGT TTA TTA GAA CAT AAA ATC TTA GAA ATG GAA
 E   I   L   K   I   H   E   K   N   S   L   L   E   H   K   I   L   E   M   E>

920              930              940              950              960              970
     •                •                •                •                •                •
GGA AAA CAC AAG GAA GAG TTG GAC ACC TTA AAG GAA GAG AAA GAG AAC CTT CAA GGC TTG
 G   K   H   K   E   E   L   D   T   L   K   E   E   K   E   N   L   Q   G   L>

980              990             1000             1010             1020             1030
     •                •                •                •                •                •
GTT ACT CGT CAA ACA TAT ATA ATC CAG GAG CTG GAA AAG CAA TTA AAC AGA GCT ACC ACC
 V   T   R   Q   T   Y   I   I   Q   E   L   E   K   Q   L   N   R   A   T   T>

1040             1050             1060             1070             1080             1090
     •                •                •                •                •                •
AAC AAC AGT GTC CTT CAG AAG CAG CAA CTG GAG CTG ATG GAC ACA GTC CAC AAC CTT GTC
 N   N   S   V   L   Q   K   Q   Q   L   E   L   M   D   T   V   H   N   L   V>
```

Fig. 5B

```
         1100          1110          1120          1130          1140          1150
          .             .             .             .             .             .
AAT CTT TGC ACT AAA GAA GTT TTA CTA AAG GGA GGA AAA AGA GAG GAA GAG AAA CCA TTT
 N   L   C   T   K   E   V   L   L   K   G   G   K   R   E   E   E   K   P   F>

1160          1170          1180          1190          1200          1210
          .             .             .             .             .             .
AGA GAC TGT GCA GAT GTA TAT CAA GCT GGT TTT AAT AAA AGT GGA ATC TAC ACT ATT TAT
 R   D   C   A   D   V   Y   Q   A   G   F   N   K   S   G   I   Y   T   I   Y>

1220          1230          1240          1250          1260          1270
          .             .             .             .             .             .
ATT AAT AAT ATG CCA GAA CCC AAA AAG GTG TTT TGC AAT ATG GAT GTC AAT GGG GGA GGT
 I   N   N   M   P   E   P   K   K   V   F   C   N   M   D   V   N   G   G   G>

1280          1290          1300          1310          1320          1330
          .             .             .             .             .             .
TGG ACT GTA ATA CAA CAT CGT GAA GAT GGA AGT CTA GAT TTC CAA AGA GGC TGG AAG GAA
 W   T   V   I   Q   H   R   E   D   G   S   L   D   F   Q   R   G   W   K   E>

1340          1350          1360          1370          1380          1390
          .             .             .             .             .             .
TAT AAA ATG GGT TTT GGA AAT CCC TCC GGT GAA TAT TGG CTG GGG AAT GAG TTT ATT TTT
 Y   K   M   G   F   G   N   P   S   G   E   Y   W   L   G   N   E   F   I   F>

1400          1410          1420          1430          1440          1450
          .             .             .             .             .             .
GCC ATT ACC AGT CAG AGG CAG TAC ATG CTA AGA ATT GAG TTA ATG GAC TGG GAA GGG AAC
 A   I   T   S   Q   R   Q   Y   M   L   R   I   E   L   M   D   W   E   G   N>

1460          1470          1480          1490          1500          1510
          .             .             .             .             .             .
CGA GCC TAT TCA CAG TAT GAC AGA TTC CAC ATA GGA AAT GAA AAG CAA AAC TAT AGG TTG
 R   A   Y   S   Q   Y   D   R   F   H   I   G   N   E   K   Q   N   Y   R   L>

1520          1530          1540          1550          1560          1570
          .             .             .             .             .             .
TAT TTA AAA GGT CAC ACT GGG ACA GCA GGA AAA CAG AGC AGC CTG ATC TTA CAC GGT GCT
 Y   L   K   G   H   T   G   T   A   G   K   Q   S   S   L   I   L   H   G   A>

1580          1590          1600          1610          1620          1630
          .             .             .             .             .             .
GAT TTC AGC ACT AAA GAT GCT GAT AAT GAC AAC TGT ATG TGC AAA TGT GCC CTC ATG TTA
 D   F   S   T   K   D   A   D   N   D   N   C   M   C   K   C   A   L   M   L>

1640          1650          1660          1670          1680          1690
          .             .             .             .             .             .
ACA GGA GGA TGG TGG TTT GAT GCT TGT GGC CCC TCC AAT CTA AAT GGA ATG TTC TAT ACT
 T   G   G   W   W   F   D   A   C   G   P   S   N   L   N   G   M   F   Y   T>

1700          1710          1720          1730          1740          1750
          .             .             .             .             .             .
GCG GGA CAA AAC CAT GGA AAA CTC AAT GGG ATA AAG TGG CAC TAC TTC AAA GGG CCC AGT
 A   G   Q   N   H   G   K   L   N   G   I   K   W   H   Y   F   K   G   P   S>

1760          1770          1780          1790          1800          1810
          .             .             .             .             .             .
TAC TCC TTA CGT TCC ACA ACT ATG ATG ATT CGA CCT TTA GAT TTT TGA AAGCGCAATGTCAGAA
 Y   S   L   R   S   T   T   M   M   I   R   P   L   D   F   *>

1820      1830      1840      1850      1860      1870      1880      1890
  .         .         .         .         .         .         .         .
GCGATTATGAAAGCAACAAAGAAATCCGGAGAAGCTGCCAGGTGAGAAACTGTTTGAAAACTTCAGAAGCAAACAATATT 1900      1910      1920      1930      1940      1950      1960      1970
  .         .         .         .         .         .         .         .
GTCTCCCTTCCAGCAATAAGTGGTAGTTATGTGAAGTCACCAAGGTTCTTGACCGTGAATCTGGAGCCGTTTGAGTTCAC 1980      1990      2000      2010      2020      2030      2040      2050
  .         .         .         .         .         .         .         .
AAGAGTCTCTACTTGGGGTGACAGTGCTCACGTGGCTCGACTATAGAAAACTCCACTGACTGTCGGGCTTTAAAAAGCGA 2060      2070      2080      2090      2100      2110      2120      2130
  .         .         .         .         .         .         .         .
AGAAACTGCTGAGCTTGCTGTGCTTCAAACTACTACTGCACCTTATTTTGGAACTATCGTAGCCAGATGATAAATATCGT

2140
  .
TAATTTC
```

Fig. 6A

```
         10        20        30        40        50        60        70        80
          •         •         •         •         •         •         •         •
GAATTCCTGGGTTGGTGTTTATCTCCTCCCAGCCTTGAGGGAGGGAACAACACTGTAGGATCTGGGGAGAGAGGAACAAA 90       100       110       120       130       140       150       160
          •         •         •         •         •         •         •         •
GGACCGTGAAAGCTGCTCTGTAAAAGCTGACACAGCCCTCCCAAGTGAGCAGGACTGTTCTTCCCACTGCAATCTGACAG 170       180       190       200       210       220       230       240
          •         •         •         •         •         •         •         •
TTTACTGCATGCCTGGAGAGAACACAGCAGTAAAAACCAGGTTTGCTACTGGAAAAAGAGGAAAGAGAAGACTTTCATTG 250       260       270       280       290       300       310       320
          •         •         •         •         •         •         •         •
ACGGACCCAGCCATGGCAGCGTAGCAGCCCTGCGTTTCAGACGGCAGCAGCTCGGGACTCTGGACGTGTGTTTGCCCTCA
```

```
          330       340       350       360       370       380
            •         •         •         •         •         •
AGTTTGCTAAGCTGCTGGTTTATTACTGAAGAAAGA ATG TGG CAG ATT GTT TTC TTT ACT CTG AGC TGT
                                      M   W   Q   I   V   F   F   T   L   S   C>

390            400            410            420            430            440
  •              •              •              •              •              •
GAT CTT GTC TTG GCC GCA GCC TAT AAC AAC TTT CGG AAG AGC ATG GAC AGC ATA GGA AAG
 D   L   V   L   A   A   A   Y   N   N   F   R   K   S   M   D   S   I   G   K>

450            460            470            480            490            500
  •              •              •              •              •              •
AAG CAA TAT CAG GTC CAG CAT GGG TCC TGC AGC TAC ACT TTC CTC CTG CCA GAG ATG GAC
 K   Q   Y   Q   V   Q   H   G   S   C   S   Y   T   F   L   L   P   E   M   D>

510            520            530            540            550            560
  •              •              •              •              •              •
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L>

570            580            590            600            610            620
  •              •              •              •              •              •
GAA TAC GAT GAC TCG GTG CAG AGG CTG CAA GTG CTG GAG AAC ATC ATG GAA AAC AAC ACT
 E   Y   D   D   S   V   Q   R   L   Q   V   L   E   N   I   M   E   N   N   T>

630            640            650            660            670            680
  •              •              •              •              •              •
CAG TGG CTA ATG AAG CTT GAG AAT TAT ATC CAG GAC AAC ATG AAG AAA GAA ATG GTA GAG
 Q   W   L   M   K   L   E   N   Y   I   Q   D   N   M   K   K   E   M   V   E>

690            700            710            720            730            740
  •              •              •              •              •              •
ATA CAG CAG AAT GCA GTA CAG AAC CAG ACG GCT GTG ATG ATA GAA ATA GGG ACA AAC CTG
 I   Q   Q   N   A   V   Q   N   Q   T   A   V   M   I   E   I   G   T   N   L>

750            760            770            780            790            800
  •              •              •              •              •              •
TTG AAC CAA ACA GCT GAG CAA ACG CGG AAG TTA ACT GAT GTG GAA GCC CAA GTA TTA AAT
 L   N   Q   T   A   E   Q   T   R   K   L   T   D   V   E   A   Q   V   L   N>

810            820            830            840            850            860
  •              •              •              •              •              •
CAG ACC ACG AGA CTT GAA CTT CAG CTC TTG GAA CAC TCC CTC TCG ACA AAC AAA TTG GAA
 Q   T   T   R   L   E   L   Q   L   L   E   H   S   L   S   T   N   K   L   E>

870            880            890            900            910            920
  •              •              •              •              •              •
AAA CAG ATT TTG GAC CAG ACC AGT GAA ATA AAC AAA TTG CAA GAT AAG AAC AGT TTC CTA
 K   Q   I   L   D   Q   T   S   E   I   N   K   L   Q   D   K   N   S   F   L>

930            940            950            960            970            980
  •              •              •              •              •              •
GAA AAG AAG GTG CTA GCT ATG GAA GAC AAG CAC ATC ATC CAA CTA CAG TCA ATA AAA GAA
 E   K   K   V   L   A   M   E   D   K   H   I   I   Q   L   Q   S   I   K   E>

990            1000           1010           1020           1030           1040
  •              •              •              •              •              •
GAG AAA GAT CAG CTA CAG GTG TTA GTA TCC AAG CAA AAT TCC ATC ATT GAA GAA CTA GAA
 E   K   D   Q   L   Q   V   L   V   S   K   Q   N   S   I   I   E   E   L   E>

1050           1060           1070           1080           1090           1100
  •              •              •              •              •              •
AAA AAA ATA GTG ACT GCC ACG GTG AAT AAT TCA GTT CTT CAA AAG CAG CAA CAT GAT CTC
 K   K   I   V   T   A   T   V   N   N   S   V   L   Q   K   Q   Q   H   D   L>
```

Fig. 6B

```
     1110           1120           1130           1140           1150           1160
      •              •              •              •              •              •
    ATG GAG ACA GTT AAT AAC TTA CTG ACT ATG ATG TCC ACA TCA AAC TCA GCT AAG GAC CCC
     M   E   T   V   N   N   L   L   T   M   M   S   T   S   N   S   A   K   D   P>

1170           1180           1190           1200           1210           1220
      •              •              •              •              •              •
    ACT GTT GCT AAA GAA GAA CAA ATC AGC TTC AGA GAC TGT GCT GAA GTA TTC AAA TCA GGA
     T   V   A   K   E   E   Q   I   S   F   R   D   C   A   E   V   F   K   S   G>

1230           1240           1250           1260           1270           1280
      •              •              •              •              •              •
    CAC ACC ACA AAT GGC ATC TAC ACG TTA ACA TTC CCT AAT TCT ACA GAA GAG ATC AAG GCC
     H   T   T   N   G   I   Y   T   L   T   F   P   N   S   T   E   E   I   K   A>

1290           1300           1310           1320           1330           1340
      •              •              •              •              •              •
    TAC TGT GAC ATG GAA GCT GGA GGA GGC GGG TGG ACA ATT ATT CAG CGA CGT GAG GAT GGC
     Y   C   D   M   E   A   G   G   G   G   W   T   I   I   Q   R   R   E   D   G>

1350           1360           1370           1380           1390           1400
      •              •              •              •              •              •
    AGC GTT GAT TTT CAG AGG ACT TGG AAA GAA TAT AAA GTG GGA TTT GGT AAC CCT TCA GGA
     S   V   D   F   Q   R   T   W   K   E   Y   K   V   G   F   G   N   P   S   G>

1410           1420           1430           1440           1450           1460
      •              •              •              •              •              •
    GAA TAT TGG CTG GGA AAT GAG TTT GTT TCG CAA CTG ACT AAT CAG CAA CGC TAT GTG CTT
     E   Y   W   L   G   N   E   F   V   S   Q   L   T   N   Q   Q   R   Y   V   L>

1470           1480           1490           1500           1510           1520
      •              •              •              •              •              •
    AAA ATA CAC CTT AAA GAC TGG GAA GGG AAT GAG GCT TAC TCA TTG TAT GAA CAT TTC TAT
     K   I   H   L   K   D   W   E   G   N   E   A   Y   S   L   Y   E   H   F   Y>

1530           1540           1550           1560           1570           1580
      •              •              •              •              •              •
    CTC TCA AGT GAA GAA CTC AAT TAT AGG ATT CAC CTT AAA GGA CTT ACA GGG ACA GCC GGC
     L   S   S   E   E   L   N   Y   R   I   H   L   K   G   L   T   G   T   A   G>

1590           1600           1610           1620           1630           1640
      •              •              •              •              •              •
    AAA ATA AGC AGC ATC AGC CAA CCA GGA AAT GAT TTT AGC ACA AAG GAT GGA GAC AAC GAC
     K   I   S   S   I   S   Q   P   G   N   D   F   S   T   K   D   G   D   N   D>

1650           1660           1670           1680           1690           1700
      •              •              •              •              •              •
    AAA TGT ATT TGC AAA TGT TCA CAA ATG CTA ACA GGA GGC TGG TGG TTT GAT GCA TGT GGT
     K   C   I   C   K   C   S   Q   M   L   T   G   G   W   W   F   D   A   C   G>

1710           1720           1730           1740           1750           1760
      •              •              •              •              •              •
    CCT TCC AAC TTG AAC GGA ATG TAC TAT CCA CAG AGG CAG AAC ACA AAT AAG TTC AAC GGC
     P   S   N   L   N   G   M   Y   Y   P   Q   R   Q   N   T   N   K   F   N   G>

1770           1780           1790           1800           1810           1820
      •              •              •              •              •              •
    ATT AAA TGG TAC TAC TGG AAA GGC TCA GGC TAT TCG CTC AAG GCC ACA ACC ATG ATG ATC
     I   K   W   Y   Y   W   K   G   S   G   Y   S   L   K   A   T   T   M   M   I>

1830       1840       1850       1860       1870       1880       1890       1900
      •          •          •          •          •          •          •          •
    CGA CCA GCA GAT TTC TAAACATCCCAGTCCACCTGAGGAACTGTCTCGAACTATTTTCAAAGACTTAAGCCCAGT
     R   P   A   D   F>

1910       1920       1930       1940       1950       1960       1970       1980
          •          •          •          •          •          •          •          •
        GCACTGAAAGTCACGGCTGCGCACTGTGTCCTCTTCCACCACAGAGGGCGTGTGCTCGGTGCTGACGGGACCCACATGCT 1990       2000       2010       2020       2030       2040       2050       2060
          •          •          •          •          •          •          •          •
        CCAGATTAGAGCCTGTAAACTTTATCACTTAAACTTGCATCACTTAACGGACCAAAGCAAGACCCTAAACATCCATAATT 2070       2080       2090       2100       2110       2120       2130       2140
          •          •          •          •          •          •          •          •
        GTGATTAGACAGAACACCTATGCAAAGATGAACCCGAGGCTGAGAATCAGACTGACAGTTTACAGACGCTGCTGTCACAA 2150       2160       2170       2180       2190       2200       2210       2220
          •          •          •          •          •          •          •          •
        CCAAGAATGTTATGTGCAAGTTTATCAGTAAATAACTGGAAAACAGAACACTTATGTTATACAATACAGATCATCTTGGA 2230       2240       2250       2260       2270       2280
          •          •          •          •          •          •
        ACTGCATTCTTCTGAGCACTGTTTATACACTGTGTAAATACCCATATGTCCTGAATTC
```

NUCLEIC ACIDS ENCODING TIE-2 LIGAND-2

This application is a continuation-in-part of U.S. application Ser. No. 373,579, filed Jan. 17, 1995, which is a continuation-in-part of U.S. Ser. No. 353,503, filed Dec. 9, 1994, which is a continuation-in-part of U.S. Ser. No. 348,492, filed Dec. 2, 1994, which is a continuation-in-part of U.S. Ser. No. 330,261 filed Oct. 27, 1994 now U.S. Pat. No. 5,521,073, which is a continuation-in-part of U.S. application Ser. No. 319,932, filed Oct. 7, 1994, the contents of each of which are hereby incorporated by reference. Throughout this application various publications are referenced. The disclosures of these publications in their entireties are hereby incorporated by reference into this application.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to novel ligands, known as the TIE-2 ligands, that bind the TIE-2 receptor, as well as to methods of making and using the TIE-2 ligands. The invention further provides nucleic acid sequences encoding TIE-2 ligands, and methods for the generation of nucleic acids encoding TIE-2 ligands and their gene products. The TIE-2 ligands, as well as nucleic acids encoding them, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. More generally, biologically active TIE-2 ligands may be used to promote the growth, survival and/or differentiation of cells expressing the TIE-2 receptor. Biologically active TIE-2 ligand may be used for the in vitro maintenance of TIE-2 receptor expressing cells in culture. Cells and tissues expressing TIE-2 receptor include, for example, cardiac and vascular endothelial cells, lens epithelium and heart epicardium. Alternatively, such ligand may be used to support cells which are engineered to express TIE-2 receptor. Further, TIE-2 ligands and their cognate receptor may be used in assay systems to identify agonists or antagonists of the TIE-2 receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosines on proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins, which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. U.S.A., 87: 8913–8917 (1990). This gene and its encoded protein are called "tie" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus tie has been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993).

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. In the mature vascular system, TIE could function in endothelial cell survival, maintenance and response to pathogenic influences.

SUMMARY OF THE INVENTION

The present invention provides for a composition comprising a TIE-2 ligand substantially free of other proteins. The invention also provides for an isolated nucleic acid molecule encoding a TIE-2 ligand. The isolated nucleic acid may be DNA, cDNA or RNA. The invention also provides for a vector comprising an isolated nucleic acid molecule encoding a TIE-2 ligand. The invention further provides for a host-vector system for the production in a suitable host cell of a polypeptide having the biological activity of a TIE-2 ligand. The suitable host cell may be bacterial, yeast, insect or mammalian. The invention also provides for a method of producing a polypeptide having the biological activity of a TIE-2 ligand which comprises growing cells of the host-vector system under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a TIE-2 ligand. The antibody may be monoclonal or polyclonal. Thus the invention further provides for therapeutic compositions comprising an antibody which specifically binds a TIE-2 ligand in a pharmaceutically acceptable vehicle. The invention also provides for a method of blocking blood vessel growth in a mammal by administering an effective amount of a therapeutic composition comprising an antibody which specifically binds a TIE-2 ligand in a pharmaceutically acceptable vehicle.

The invention further provides for therapeutic compositions comprising a TIE-2 ligand in a pharmaceutically acceptable vehicle. The invention also provides for a method of promoting neovascularization in a patient by administering an effective amount of a therapeutic composition comprising a TIE-2 ligand in a pharmaceutically acceptable vehicle. In one embodiment, the method may be used to promote wound healing. In another embodiment, the method may be used to treat ischemia.

Alternatively, the invention provides that a TIE-2 ligand may be conjugated to a cytotoxic agent and a therapeutic composition prepared therefrom. The invention further provides for a receptor body which specifically binds a TIE-2 ligand. The invention further provides for therapeutic compositions comprising a receptor body which specifically binds a TIE-2 ligand in a pharmaceutically acceptable vehicle. The invention also provides for a method of blocking blood vessel growth in a mammal by administering an effective amount of a therapeutic composition comprising a receptor body which specifically binds a TIE-2 ligand in a pharmaceutically acceptable vehicle.

The invention also provides for a TIE-2 receptor antagonist, known as TIE-2 ligand 2, as well as a method of inhibiting TIE-2 ligand biological activity in a mammal comprising administering to the mammal an effective amount of a TIE-2 antagonist. According to the invention, the antagonist may be an antibody or other molecule capable of specifically binding either TIE-2 ligand or TIE-2 receptor. For example, the antagonist may be a TIE-2 receptorbody.

BRIEF DESCRIPTION OF THE FIGURES

FIG. 1A: embryos treated with EHK-1 RB (rEHK-1 ecto/h IgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIGS. 4A and 4B—Nucleic acid and deduced amino acid (single letter code) sequences of human TIE-2 ligand from clone λgt10 encoding htie-2 ligand 1 (SEQ. ID. NOS. 1 & 2).

FIGS. 5A and 5B—Nucleic acid and deduced amino acid (single letter code) sequences of human TIE-2 ligand from T98G clone (SEQ. ID. NOS. 3 & 4).

FIGS. 6A and 6B—Nucleic acid and deduced amino acid (single letter code) sequences of human TIE-2 ligand from clone pBluescript KS encoding human TIE 2 ligand 2 (SEQ. ID. NOS. 5 & 6).

DETAILED DESCRIPTION OF THE INVENTION

Figure 1A:
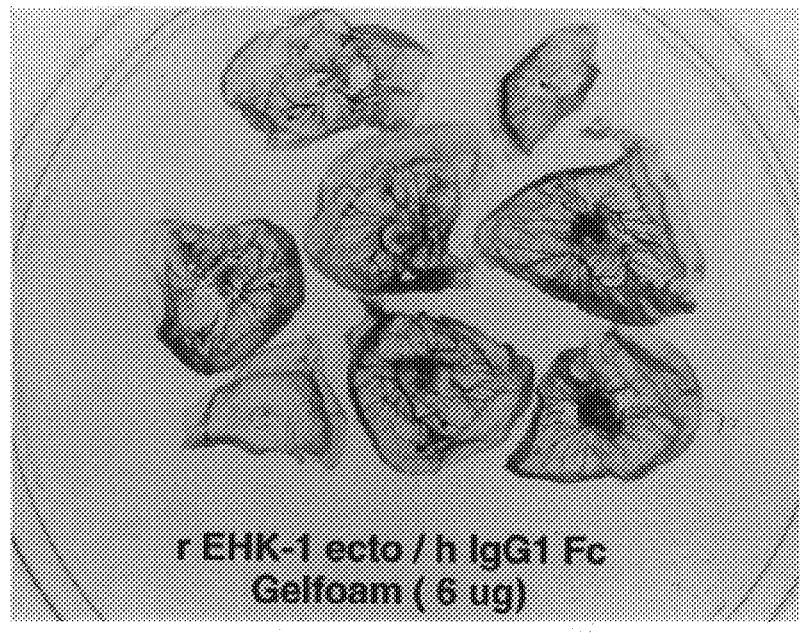
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 μg of RB was inserted immediately under the CAM of 1-day chick embryos. After 3 further days of incubation, 4 day old embryos and surrounding CAM were removed and examined.

As described in greater detail below, applicants have isolated, by expression cloning, a novel ligand that binds the TIE-2 receptor. The present invention comprises a TIE-2 ligand as well as its amino acid sequence and also functionally equivalent molecules in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

The present invention also encompasses the nucleotide sequence that encodes the protein described herein as TIE-2 ligand 1, as well as cells which are genetically engineered to produce the protein, by e.g. transfection, transduction, infection, electroporation, or microinjection of nucleic acid encoding the TIE-2 ligand 1 described herein in a suitable expression vector.

The present invention further encompasses the nucleotide sequence that encodes the protein described herein as TIE-2 ligand 2, as well as cells which are genetically engineered to produce the protein, by e.g. transfection, transduction, infection, electroporation, or microinjection of nucleic acid encoding the TIE-2 ligand 2 described herein in a suitable expression vector.

One skilled in the art will also recognize that the present invention encompasses DNA and RNA sequences that hybridize to a deduced TIE-2 ligand encoding sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a sequence deduced from an amino acid sequence of a TIE-2 ligand prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds the TIE-2 receptor.

Any of the methods known to one skilled in the art for the insertion of DNA fragments into a vector may be used to construct expression vectors encoding TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding a TIE-2 ligand or peptide fragments thereof may be regulated by a second nucleic acid sequence so that the protein or peptide is expressed in a host transformed with the recombinant DNA molecule. For example, expression of a TIE-2 ligand described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothioein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells (Hanahan, Nature 315:115–122 (1985)), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding a TIE-2 ligand to modulate its expression. (Ecker, U.S. Pat. No. 5,166,195, issued Nov. 24, 1992).

Thus, according to the invention, expression vectors capable of being replicated in a bacterial or eukaryotic host comprising a nucleic acid encoding a TIE-2 ligand as described herein, are used to transfect a host and thereby direct expression of such nucleic acid to produce the TIE-2 ligand, which may then be recovered in a biologically active form. As used herein, a biologically active form includes a form capable of binding to the TIE-2 receptor and causing a biological response such as a differentiated function or influencing the phenotype of the cell expressing the receptor. Such biologically active forms would, for example, induce phosphorylation of the tyrosine kinase domain of the TIE-2 receptor.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE-2 ligand encoding gene. In the second approach, the recombinant vector/host system can be identified and selected based upon the presence or absence of certain "marker" gene functions (ea., thymidine kinase activity, resistance to antibiotics, transformation phenotype, occlusion body formation in baculovirus, etc.) caused by the insertion of foreign genes in the vector. For example, if a nucleic acid encoding a TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE-2 ligand gene product, for example, by binding of the ligand to the TIE-2 receptor or portion thereof which may be tagged with, for example, a detectable antibody or portion thereof or by binding to antibodies produced against the TIE-2 ligand protein or a portion thereof. Cells of the present invention may transiently or, preferably, constitutively and permanently express TIE-2 ligands as described herein. In the fourth approach, DNA nucleotide primers can be prepared corresponding to a tie-2 specific DNA sequence. These primers could then be used to PCR a tie-2 gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. For example, and not by way of limitation, the ligand may be recovered from cells either as soluble proteins or as inclusion bodies, from which they may be extracted quantitatively by 8M guanidinium hydrochloride and dialysis. In order to further purify the ligand, conventional ion exchange chromatography, hydrophobic interaction chromatography, reverse phase chromatography or gel filtration may be used.

In additional embodiments of the invention, a recombinant TIE-2 ligand encoding gene may be used to inactivate or "knock out" the endogenous gene by homologous recombination, and thereby create a TIE-2 ligand deficient cell, tissue, or animal. For example, and not by way of limitation, the recombinant TIE-2 ligand encoding gene may be engineered to contain an insertional mutation, for example the neo gene, which would inactivate the native TIE-2 ligand encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE-2 ligand encoding gene may then be identified, e.g. by Southern blotting, PCR detection, Northern blotting or assay of expression. Cells lacking an intact TIE-2 ligand encoding gene may then be fused to early embryo cells to generate transgenic animals deficient in such ligand. Such an animal may be used to define specific in vivo processes, normally dependent upon the ligand.

The present invention also provides for antibodies to the TIE-2 ligands described herein which are useful for detection of the ligands in, for example, diagnostic applications. For preparation of monoclonal antibodies directed toward TIE-2 ligand, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e g, Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the TIE-2 ligands described herein. For the production of antibody, various host animals can be immunized by injection with a TIE-2 ligand, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected TIE-2 ligand epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of a TIE-2 ligand in a biological sample by a) contacting the biological sample with at least one antibody which specifically binds the TIE-2 ligand so that the antibody forms a complex with any TIE-2 ligand present in the sample; and b) measuring the amount of the complex and thereby measuring the amount of the TIE-2 ligand in the biological sample.

The invention further encompasses an assay for measuring the amount of TIE-2 receptor in a biological sample by a) contacting the biological sample with at least one ligand of the invention so that the ligand forms a complex with the TIE-2 receptor; and b) measuring the amount of the complex and thereby measuring the amount of the TIE-2 receptor in the biological sample.

The present invention also provides for the utilization of a TIE-2 ligand to support the survival and/or growth and/or differentiation of TIE-2 receptor expressing cells. Thus, the ligand may be used as a supplement to support, for example, endothelial cells in culture.

Further, the discovery by applicants of a cognate ligand for the TIE-2 receptor enables the utilization of assay systems useful for the identification of agonists or antagonists of the TIE-2 receptor. Such assay systems would be useful in identifying molecules capable of promoting or inhibiting angiogenesis. For example, in one embodiment, antagonists of the TIE-2 receptor may be identified as test molecules that are capable of interfering with the interaction of the TIE-2 receptor with a biologically active TIE-2 ligand. Such antagonists are identified by their ability to 1) block the binding of a biologically active TIE-2 ligand to the receptor as measured, for example, using BIAcore biosensor technology (BIAcore; Pharmacia Biosensor, Piscataway, N.J.); or 2) block the ability of a biologically active TIE-2 ligand to cause a biological response. Such biological responses include, but are not limited to, phosphorylation of the TIE-2 receptor or downstream components of the TIE-2 signal transduction pathway, or survival, growth or differentiation of TIE-2 receptor bearing cells.

In one embodiment, cells engineered to express the TIE-2 receptor may be dependent for growth on the addition of TIE-2 ligand. Such cells provide useful assay systems for identifying additional agonists of the TIE-2 receptor, or antagonists capable of interfering with the activity of TIE-2 ligand on such cells. Alternatively, autocrine cells, engineered to be capable of co-expressing both TIE-2 ligand and receptor, may provide useful systems for assaying potential agonists or antagonists.

Therefore, the present invention provides for introduction of the TIE-2 receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of the TIE-2 receptor into a fibroblast cell line (e.g., NIH3T3 cells) thus such a receptor which does not normally mediate proliferative responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE-2 ligand, thus creating an autocrine system useful for assaying for molecules that act as antagonists/agonists of this interaction. Thus, the present invention provides for host cells comprising nucleic acid encoding TIE-2 ligand and nucleic acid encoding TIE-2 receptor.

The TIE-2 receptor/TIE-2 ligand interaction also provides a useful system for identifying small molecule agonists or antagonists of the TIE-2 receptor. For example, fragments, mutants or derivatives of a TIE-2 ligand may be identified that bind the TIE-2 receptor but do not induce biological activity. Alternatively, the characterization of a TIE-2 ligand enables the determination of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to the TIE-2 receptor may be measured in a number of ways. For example, the actual binding of test molecule to cells expressing tie-2 may be detected or measured, by detecting or measuring (i) test molecule bound to the surface of intact cells; (ii) test molecule cross-linked to TIE-2 protein in cell lysates; or (iii) test molecule bound to TIE-2 in vitro. The specific interaction between test molecule and TIE-2 may be evaluated by using reagents that demonstrate the unique properties of that interaction.

As a specific, nonlimiting example, the methods of the invention may be used as follows. Consider a case in which the TIE-2 ligand in a sample is to be measured. Varying dilutions of the sample (the test molecule), in parallel with a negative control (NC) containing no TIE-2 ligand activity, and a positive control (PC) containing a known amount of a TIE-2 ligand, may be exposed to cells that express tie-2 in the presence of a detectably labeled TIE-2 ligand (in this example, radioiodinated ligand). The amount of TIE-2 ligand in the test sample may be evaluated by determining the amount of $^{125}$I-labeled TIE-2 ligand that binds to the controls and in each of the dilutions, and then comparing the sample values to a standard curve. The more TIE-2 ligand in the sample, the less $^{125}$I-ligand that will bind to TIE-2.

The amount of $^{125}$I-ligand bound may be determined by measuring the amount of radioactivity per cell, or by cross-linking the TIE-2 ligand to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE-2 ligand/TIE-2 receptor. The specific test molecule/TIE-2 interaction may further be tested by adding to the assays various dilutions of an unlabeled control ligand that does not bind the TIE-2 receptor and therefore should have no substantial affect on the competition between labeled TIE-2 ligand and test molecule for TIE-2 binding. Alternatively, a molecule known to be able to disrupt TIE-2 ligand/TIE-2 binding, such as, but not limited to, anti-TIE-2 antibody, or TIE-2 receptorbody as described herein, may be expected to interfere with the competition between $^{125}$I-TIE-2 ligand and test molecule for TIE-2 receptor binding.

Detectably labeled TIE-2 ligand includes, but is not limited to, TIE-2 ligand linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

Alternatively, the specific binding of test molecule to TIE-2 may be measured by evaluating the secondary biological effects of TIE-2 ligand/TIE-2 receptor binding, including, but not limited to, cell growth and/or differentiation or immediate early gene expression or phosphorylation of TIE-2. For example, the ability of the test molecule to induce differentiation can be tested in cells that lack tie-2 and in comparable cells that express tie-2; differentiation in tie-2 expressing cells but not in comparable cells that lack tie-2 would be indicative of a specific test molecule/TIE-2 interaction. A similar analysis could be performed by detecting immediate early gene (e.g. fos and jun) induction in tie-2-minus and ti-2-plus cells, or by detecting phosphorylation of TIE-2 using standard phosphorylation assays known in the art. Such analysis might be useful in identifying agonists or antagonists that do not competitively bind to TIE-2.

Similarly, the present invention provides for a method of identifying a molecule that has the biological activity of a TIE-2 ligand comprising (i) exposing a cell that expresses tie-2 to a test molecule and (ii) detecting the specific binding of the test molecule to TIE-2 receptor, in which specific binding to TIE-2 positively correlates with TIE-2 like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-2-minus or engineered to be tie-2-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE-like activity or identifying a molecule as having such activity comprising (i) exposing a test molecule to a TIE-2 receptor protein in vitro under conditions that permit binding to occur and (ii) detecting binding of the test molecule to the TIE-2 protein, in which binding of test molecule to TIE-2 correlates with TIE-like activity. According to such methods, the TIE-2 may or may not be substantially purified, may be affixed to a solid support (e.g. as an affinity column or as an ELISA assay), or may be incorporated into an artificial membrane. Binding of test molecule to TIE-2 may be evaluated by any method known in the art. In preferred embodiments, the binding of test molecule may be detected or measured by evaluating its ability to compete with detectably labeled known TIE-2 ligands for TIE-2 receptor binding.

The present invention also provides for a method of detecting the ability of a test molecule to function as an antagonist of TIE-like activity comprising detecting the ability of the molecule to inhibit an effect of TIE ligand binding to TIE-2 on a cell that expresses tie-2. Such an antagonist may or may not interfere with TIE-2 ligand/TIE-2 receptor binding. Effects of TIE-2 ligand binding to TIE-2 receptor are preferably biological or biochemical effects, including, but not limited to, cell survival or proliferation, cell transformation, immediate early gene induction, or TIE-2 phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of TIE ligand which has been Myc-tagged may then be introduced to the well and any tagged TIE ligand which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or TIE ligand is covalently attached to a solid support (e.g. carboxymethyl dextran on a gold surface), one of skill in the art would be able to determine if the blocker molecule is binding specifically to the ligand or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE-2 receptor.

Because TIE-2 receptor has been identified in association with endothelial cells and, as demonstrated herein, blocking of the ligand appears to prevent vascularization, applicants have demonstrated that the TIE-2 ligand will be useful for the induction of vascularization in diseases or disorders where such vascularization is indicated. Such diseases or disorders would include wound healing, ischaemia and diabetes. On the other hand, antagonists of the TIE-2 receptor, such as receptorbodies as described herein in Examples 2 and 3, and TIE-2 ligand 2 as described in Example 9, would be useful to prevent or attenuate vascularization, thus preventing or attenuating, for example, tumor growth.

The present invention also provides for pharmaceutical compositions comprising the TIE-2 ligands described herein, peptide fragments thereof, or derivatives in a pharmacologically acceptable vehicle. The TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention further provides for an isolated and purified nucleic acid molecule comprising a nucleic acid sequence encoding a human TIE-2 ligand, wherein the nucleic acid sequence is selected from the group consisting of:
(a) the nucleic acid sequence comprising the coding region of the human TIE-2 ligand as set forth in FIGS. 6A and 6B (SEQ. ID. NO. 5).
(b) a nucleic acid sequence that hybridizes under moderately stringent conditions to the nucleic acid sequence of (a) and which encodes a TIE-2 ligand that binds TIE-2 receptor; and
(c) a nucleic acid sequence that is degenerate as a result of the genetic code to a nucleic acid sequence of (a) or (b), and which encodes a TIE-2 ligand that binds TIE-2 receptor.

The present invention further provides for an isolated and purified human TIE-2 ligand encoded by an isolated nucleic acid molecule of the invention. The invention also provides a vector which comprises an isolated nucleic acid molecule comprising a nucleic acid sequence encoding a human TIE-2 ligand. In one embodiment, the vector is designated as pBluescript KS encoding human TIE 2 ligand 2 ATCC Accession No. 75963.

The invention further provides for an expression vector comprising a DNA molecule encoding a human TIE-2 ligand, wherein the DNA molecule is operatively linked to an expression control sequence. The invention also provides a host-vector system for the production of a polypeptide having the biological activity of a human TIE-2 ligand which comprises the expression vector of the invention in a suitable host cell. In one embodiment, the suitable host cell may be a bacterial cell, yeast cell, insect cell, or mammalian cell. The invention further provides for a method of producing a polypeptide having the activity of a biologically active TIE-2 ligand which comprises growing cells of the host-vector system of the invention, under conditions permitting production of the polypeptide and recovering the polypeptide so produced.

The invention herein described of an isolated nucleic acid molecule encoding a TIE-2 ligand further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a human TIE-2 ligand and a cytotoxic agent conjugated thereto. In one embodiment, the cytotoxic agent may be a radioisotope or toxin.

The invention also provides for an antibody which specifically binds a human TIE-2 ligand. The antibody may be monoclonal or polyclonal. The invention further provides for a method of purifying a human TIE-2 ligand comprising:
a) coupling at least one TIE-2 binding substrate to a solid matrix;
b) incubating the substrate of a) with a cell lysate so that the substrate forms a complex with any human TIE-2 ligand in the cell lysate;
c) washing the solid matrix; and
d) eluting the human TIE-2 ligand from the coupled substrate.

The substrate may be any substance that specifically binds the human TIE-2 ligand. In one embodiment, the substrate is selected from the group consisting of anti-TIE-2 ligand antibody, TIE-2 receptor and TIE-2 receptorbody. The invention further provides for a receptorbody which specifically binds a human TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a human TIE-2 ligand in a pharmaceutically acceptable vehicle, as well as a method of promoting neovascularization in a patient comprising administering to the patient an effective amount of the therapeutic composition.

In addition, the present invention provides for a method for identifying a cell which expresses TIE-2 receptor which comprises contacting a cell with a detectably labeled TIE-2 ligand, under conditions permitting binding of the detectably labeled ligand to the TIE-2 receptor and determining whether the detectably labeled ligand is bound to the TIE-2 receptor, thereby identifying the cell as one which expresses TIE-2 receptor. The present invention also provides for a therapeutic composition comprising a TIE-2 ligand and a cytotoxic agent conjugated thereto. The cytotoxic agent may be a radioisotope or toxin.

The invention also provides a method of detecting expression of TIE-2 ligand by a cell which comprises obtaining mRNA from the cell, contacting the mRNA so obtained with a labelled nucleic acid molecule encoding a TIE-2 ligand, under hybridizing conditions, determining the presence of mRNA hybridized to the labelled molecule, and thereby detecting the expression of the TIE-2 ligand in the cell.

The invention further provides a method of detecting expression of a TIE-2 ligand in tissue sections which comprises contacting the tissue sections with a labelled nucleic acid molecule encoding a TIE-2 ligand, under hybridizing conditions, determining the presence of mRNA hybridized to the labelled molecule, and thereby detecting the expression of the TIE-2 ligand in tissue sections.

EXAMPLE 1

IDENTIFICATION OF THE ABAE CELL LINE AS REPORTER CELLS FOR THE TIE-2 RECEPTOR

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors, PMSF and aprotinin. Insoluble debris was removed from the cell lysates by centrifugation at 14,000×G for 10 minutes, at 4° C. and the supernatants were subjected to immune-precipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2-protein was visualized by incubation of the membrane with HRP-linked secondary antisera followed by treatment with ECL reagent (Amersham).

EXAMPLE 2

CLONING AND EXPRESSION OF TIE-2 RECEPTORBODY FOR AFFINITY-BASED STUDY OF TIE-2 LIGAND INTERACTIONS

An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-Notl fragment into the baculovirus transfer plasmid pVL1393. Plasmid DNA purified by cesium chloride density gradient centrifugation was recombined into viral DNA by mixing 3 µg of plasmid DNA with 0.5 µg of Baculo-Gold DNA (Pharminigen), followed by introduction into liposomes using 30 µg Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual.* 1992, New York: W. H. Freeman) except that the agarose overlay contained 125 µg/mL X-gal (5-bromo-4-chloro-3-indolyl-β-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 µg/mL MTT (3-[4,5-dimethylthiazol-2-yl]2,5, diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptor body) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10$^6$ cells per mL), concentrated by centrifugation, and infected with 5 plaque forming units of vTIE-2 Receptor Body per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions. Culture medium from vTIE-2 Receptor Body-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5M NaCl until the absorbance at 280 nm decreased to baseline. The column was washed in PBS and eluted with 0.5M acetic acid. Column fractions were immediately neutralized by eluting into tubes containing 1M Tris pH 9. The peak fractions containing the TIE-2 RB were pooled and dialyzed versus PBS.

EXAMPLE 3

DEMONSTRATION THAT TIE-2 HAS A CRITICAL ROLE IN DEVELOPMENT OF THE VASCULATURE

Given the absence of a known ligand for TIE-2 receptor, it was reasoned that it might be possible to gain insight into the function of TIE-2 by introduction of "excess" soluble TIE-2 receptor body (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extraembryonically-derived endothelial cells, which provide the major source for endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intraembryonically-derived vascular elements.

Figure 1B:
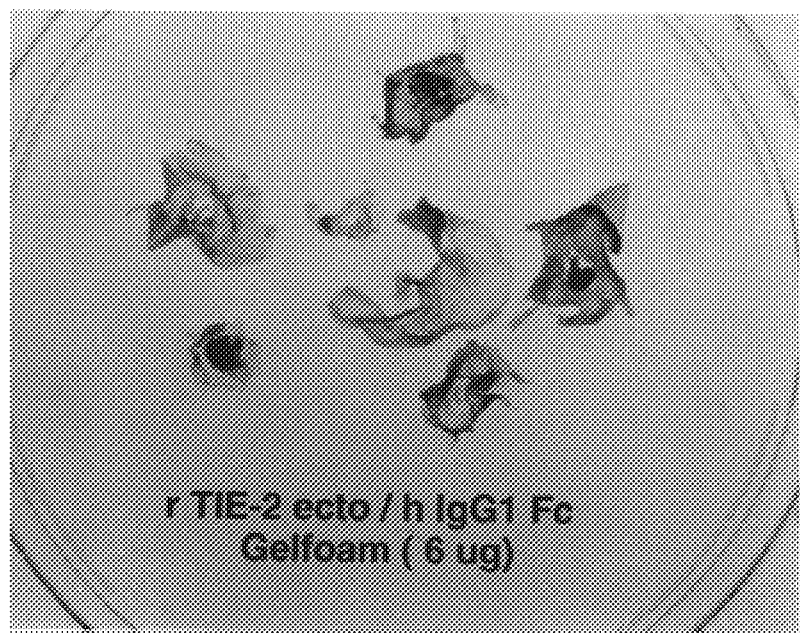

Newly fertilized chicken eggs obtained from Spafas, Inc. (Boston, Mass.) were incubated at 99.5° F., 55% RH. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm. in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

IDENTIFICATION OF A TIE-2-SPECIFIC BINDING ACTIVITY IN CONDITIONED MEDIUM FROM THE ras ONCOGENE-TRANSFORMED C2C12 MOUSE MYOBLAST CELL LINE Screening of ten-fold-concentrated cell-conditioned media (10× CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras-transformed fibroblast cell line), human glioblastoma T98G and the human neuroblastoma cell line known as SHEP-1.

The C2C12-ras 10× CCM originated from a stably-transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10× CCM was made by plating the cells at 60% confluence in a serum free defined media for 12 hours. (Zhan and Goldfarb, Mol. Cell. Biol. 6: 3541–3544 (1986)); Zhan, et al. Oncogene 1: 369–376 (1987)). The medium was discarded and replaced with fresh DMEM/Q/P-S for 24 hours. This medium was harvested and cells were refed fresh DMEM/Q/P-S, which was also harvested after a further 24 hours. These CCM were supplemented with the protease inhibitors PMSF (1 mM) and aprotinin (10 µg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10× CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0M ethanolamine (pH 8.5). A negative control surface of the EHK-1 receptorbody was prepared in a similar manner. The running buffer used in the system was HBS (10 mM Hepes, 3.4 mM edta, 150 mM NaCl, 0.005% P20 surfactant, pH 7.4). The 10× CCM samples were centrifuged for 15 min at 4 C. and further clarified using a sterile, low protein-binding 0.45 µm filter (Millipore; Bedford, Mass.). Dextran (2 mg/ml) and P20 surfactant (0.005%) were added to each CCM sample. Aliquots of 40 µL were injected across the immobilized surface (either TIE-2 or EHK-1) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-µL pulse of 3M $MgCl_2$. The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM CONTAINS AN ACTIVITY THAT INDUCES TYROSINE PHOSPHORYLATION OF TIE-2 RECEPTOR C2C12-ras 10× CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10× CCM was done as follows. The medium of ABAE cells starved as described above was removed and replaced with either defined medium or 10× CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100×increase in TIE-2 phosphorylation. This activity was almost totally depleted by pre-incubation of the C2C12-ras 10× CCM for 90 minutes at room temperature with 13 ug of TIE-2 RB coupled to protein G-Sepharose beads. Medium incubated with protein G Sepharose alone was not depleted of this phosphorylating activity.

EXAMPLE 6

EXPRESSION CLONING OF TIE-2 LIGAND

Figure 2:
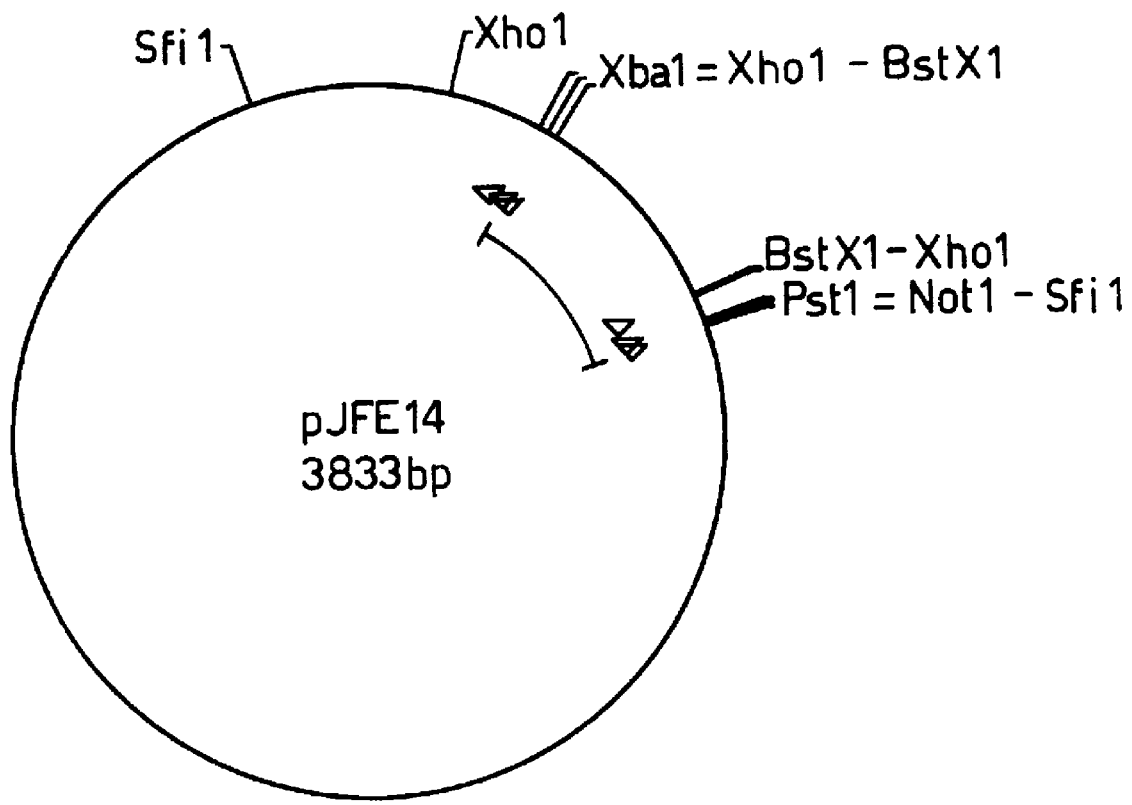
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells per 100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours. Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2-RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

ISOLATION AND SEQUENCING OF FULL LENGTH cDNA CLONE ENCODING HUMAN TIE-2 LIGAND

Figure 3:
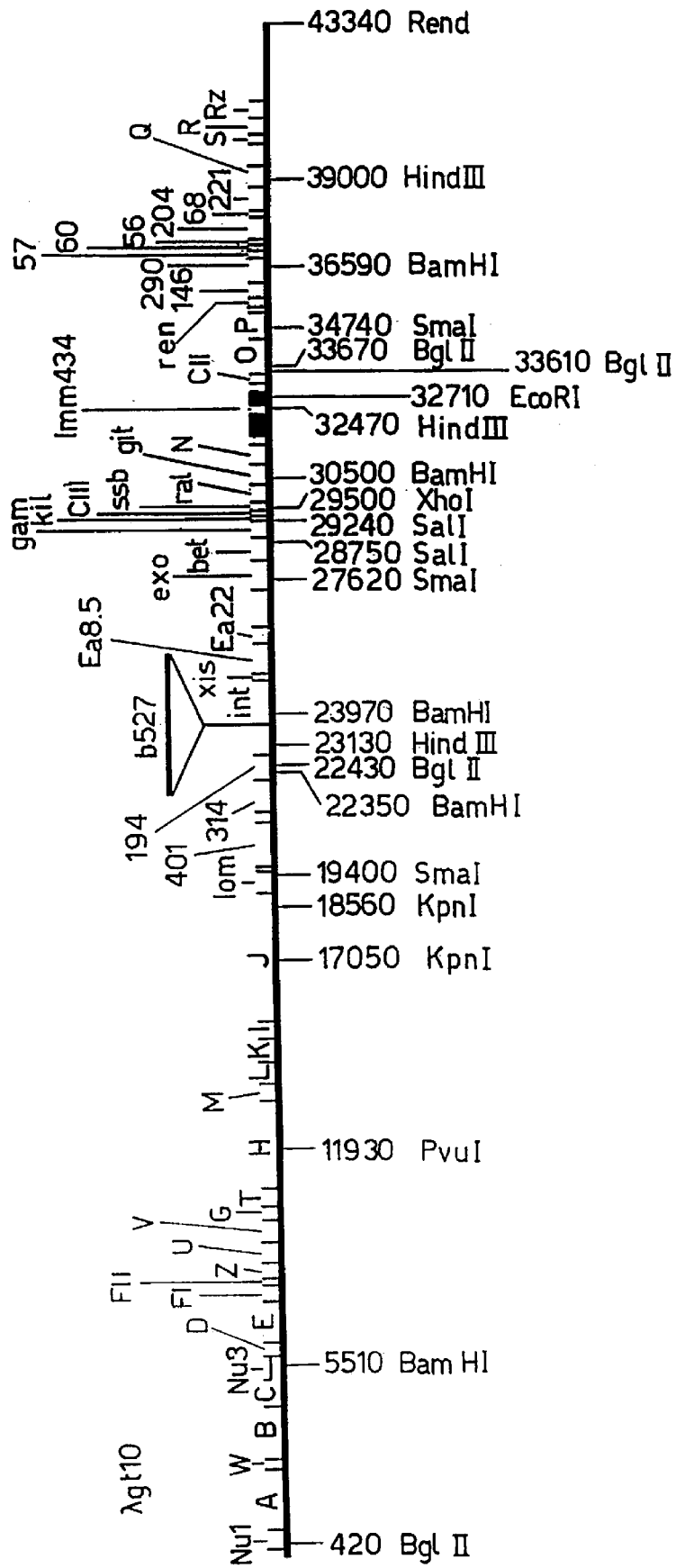
FIG. 3—Restriction map of λgt10.

A human fetal lung cDNA library in lambda gt-10 (see FIG. 3) was obtained from Clontech Laboratories, Inc. (Palo Alto, Calif.). Plaques were plated at a density of $1.25 \times 10^6$/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2× SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning human TIE-2 ligand into a mammalian expression vector

The clone λgt10 encoding htie-2 ligand 1 contains an EcoRI site located 490 base pairs downstream from the start of the coding sequence for the human tie-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

Sequencing of human TIE-2 ligand

The coding region from the clone λgt10 encoding htie-2 ligand 1 was sequenced using the ABI 373A DNA sequencer and Taq Dyedeoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in FIG. 4A and 4B (SEQ. ID. NOS. 1 & 2).

In addition, full length human TIE-2 ligand cDNA clones were obtained by screening a human glioblastoma T98G cDNA library in the pJFE14 vector. Clones encoding human tie-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dyedeoxy Terminator Cycle Sequencing Kit (Applied Biosystems, Inc., Foster City, Calif.). This sequence was nearly identical to that of clone λgt10 encoding htie-2 ligand 1. As shown in FIGS. 4A and 4B (SEQ. ID. NOS. 1 & 2) the clone λgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIGS. 5A and 5B (SEQ. ID. NOS. 3 & 4) sets forth the nucleotide and deduced amino acid sequence of human TIE-2 ligand from the T98G clone.

EXAMPLE 8

ISOLATION AND SEQUENCING OF SECOND FULL LENGTH cDNA CLONE A ENCODING HUMAN TIE-2 LIGAND

A human fetal lung cDNA library in lambda gt-10 (see FIG. 3) was obtained from Clontech Laboratories, Inc. (Palo Alto, Calif.). Plaques were plated at a density of $1.25 \times 10^6$/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at low stringency (2×SSC, 55° C.) with probes made to the human tie 2 L-1 sequence. One of the duplicate filters was probed with a 5' probe, encoding amino acids 25–265 of human tie 2L-1 as set forth in FIGS. 4A and 4B (SEQ. ID. NOS. 1 & 2). The second duplicate filter was probed with a 3' probe, encoding amino acids 282–498 of human tie 2 L-1 sequence (see FIGS. 4A and 4B (SEQ. ID. NOS. 1 & 2). Both probes were hybridized at 55 C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse tie2L (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of $1.0 \times 10^6$ cells per 100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells per 100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2-RB. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptor body.

One of skill in the art will readily see that the described methods may be used to further identify other related members of the TIE ligand family.

Sequencing of second human TIE-2 ligand

The coding region from the clone pBluescript KS encoding human TIE-2 ligand 2 was sequenced using the ABI 373A DNA sequencer and Taq Dyedeoxy Terminator Cycle Sequencing Kit (Applied Biosystems, Inc., Foster City, Calif.). The nucleotide and deduced amino acid sequence of human TIE-2 ligand from the clone pBluescript KS encoding human TIE-2 ligand 2 is shown in FIGS. 6A and 6B (SEQ. ID. NOS. 5 & 6).

EXAMPLE 9

TIE-2 LIGAND 2 IS A RECEPTOR ANTAGONIST

Conditioned media from COS cells expressing either TIE-2 ligand 2 (TL2) or TIE-2 ligand 1 (TL1) were compared for their ability to activate TIE-2 receptors naturally present in a human endothelial cell line.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. U.S.A. 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
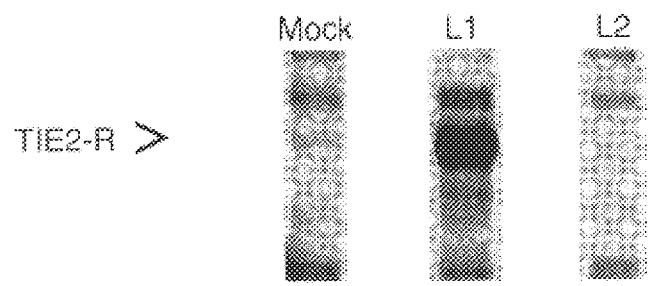
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 30° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
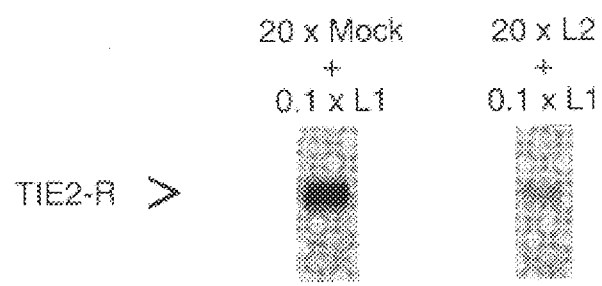
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).

Semi-confluent HAEC cells were serum-starved as described above and then incubated for 3 min., at 37° C. with 1–2 ml. of 20× COS/JFE14-TL2 conditioned medium. Control plates were treated with 20× COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20× COS/JFE14-TL1 medium diluted to 2×, 0.5×, 0.1×, or 0.02× by addition of 20× COS/JFE14-alone medium. An assay of the initial 20× TL1 and 20× TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane 2) antagonizes the subsequent ability of dilute TIE-2 ligand 1 to activate the TIE-2 receptor (TIE2-R).

These data indicate that, unlike TL1, TL2 was not able to stimulate TIE-2 receptor kinase activity in HAEC cells. Furthermore, pre-incubation of the endothelial cells with high concentrations of TL2 followed by addition of TL1 blocked the ability of TL1 to stimulate the TIE-2 receptor, indicating that TL2 is a TIE-2 receptor antagonist.

DEPOSITS

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptor body was deposited with the ATCC on Oct. 7, 1994 and designated as "vTIE-2 receptor body" under ATCC Accession No. VR2484. A lambda phage vector containing human tie-2 ligand DNA was deposited with the ATCC on Oct. 26, 1994 and designated as λgt10 encoding htie-2 ligand 1 under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2149 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 310..1806

( x i ) SEQUENCE DESCRIPTION: SEQ ID NO:1:

```
CAGCTGACTC  AGGCAGGCTC  CATGCTGAAC  GGTCACACAG  AGAGGAAACA  ATAAATCTCA       60

GCTACTATGC  AATAAATATC  TCAAGTTTTA  ACGAAGAAAA  ACATCATTGC  AGTGAAATAA      120

AAAATTTTAA  AATTTTAGAA  CAAAGCTAAC  AAATGGCTAG  TTTTCTATGA  TTCTTCTTCA      180

AACGCTTTCT  TTGAGGGGGA  AAGAGTCAAA  CAAACAAGCA  GTTTTACCTG  AAATAAAGAA      240

CTAGTTTTAG  AGGTCAGAAG  AAAGGAGCAA  GTTTTGCGAG  AGGCACGGAA  GGAGTGTGCT      300

GGCAGTACA  ATG  ACA  GTT  TTC  CTT  TCC  TTT  GCT  TTC  CTC  GCT  GCC  ATT   348
           Met Thr Val Phe Leu Ser Phe Ala Phe Leu Ala Ala Ile
            1              5                   10

CTG ACT CAC ATA GGG TGC AGC AAT CAG CGC CGA AGT CCA GAA AAC AGT            396
Leu Thr His Ile Gly Cys Ser Asn Gln Arg Arg Ser Pro Glu Asn Ser
     15              20                  25

GGG AGA AGA TAT AAC CGG ATT CAA CAT GGG CAA TGT GCC TAC ACT TTC            444
Gly Arg Arg Tyr Asn Arg Ile Gln His Gly Gln Cys Ala Tyr Thr Phe
 30              35                  40                      45

ATT CTT CCA GAA CAC GAT GGC AAC TGT CGT GAG AGT ACG ACA GAC CAG            492
Ile Leu Pro Glu His Asp Gly Asn Cys Arg Glu Ser Thr Thr Asp Gln
                 50                  55                  60

TAC AAC ACA AAC GCT CTG CAG AGA GAT GCT CCA CAC GTG GAA CCG GAT            540
Tyr Asn Thr Asn Ala Leu Gln Arg Asp Ala Pro His Val Glu Pro Asp
             65                  70                  75

TTC TCT TCC CAG AAA CTT CAA CAT CTG GAA CAT GTG ATG GAA AAT TAT            588
Phe Ser Ser Gln Lys Leu Gln His Leu Glu His Val Met Glu Asn Tyr
         80                  85                  90

ACT CAG TGG CTG CAA AAA CTT GAG AAT TAC ATT GTG GAA AAC ATG AAG            636
Thr Gln Trp Leu Gln Lys Leu Glu Asn Tyr Ile Val Glu Asn Met Lys
     95                 100                 105

TCG GAG ATG GCC CAG ATA CAG CAG AAT GCA GTT CAG AAC CAC ACG GCT            684
Ser Glu Met Ala Gln Ile Gln Gln Asn Ala Val Gln Asn His Thr Ala
110                 115                 120                 125
```

| | | | | | | | | | | | | | | | | |
|---|---|---|---|---|---|---|---|---|---|---|---|---|---|---|---|---|
| ACC | ATG | CTG | GAG | ATA | GGA | ACC | AGC | CTC | CTC | TCT | CAG | ACT | GCA | GAG | CAG | 732 |
| Thr | Met | Leu | Glu | Ile | Gly | Thr | Ser | Leu | Leu | Ser | Gln | Thr | Ala | Glu | Gln | |
| | | | 130 | | | | 135 | | | | | | | 140 | | |
| ACC | AGA | AAG | CTG | ACA | GAT | GTT | GAG | ACC | CAG | GTA | CTA | AAT | CAA | ACT | TCT | 780 |
| Thr | Arg | Lys | Leu | Thr | Asp | Val | Glu | Thr | Gln | Val | Leu | Asn | Gln | Thr | Ser | |
| | | | 145 | | | | 150 | | | | | 155 | | | | |
| CGA | CTT | GAG | ATA | CAG | CTG | CTG | GAG | AAT | TCA | TTA | TCC | ACC | TAC | AAG | CTA | 828 |
| Arg | Leu | Glu | Ile | Gln | Leu | Leu | Glu | Asn | Ser | Leu | Ser | Thr | Tyr | Lys | Leu | |
| | | 160 | | | | | 165 | | | | | 170 | | | | |
| GAG | AAG | CAA | CTT | CTT | CAA | CAG | ACA | AAT | GAA | ATC | TTG | AAG | ATC | CAT | GAA | 876 |
| Glu | Lys | Gln | Leu | Leu | Gln | Gln | Thr | Asn | Glu | Ile | Leu | Lys | Ile | His | Glu | |
| | 175 | | | | | 180 | | | | | 185 | | | | | |
| AAA | AAC | AGT | TTA | TTA | GAA | CAT | AAA | ATC | TTA | GAA | ATG | GAA | GGA | AAA | CAC | 924 |
| Lys | Asn | Ser | Leu | Leu | Glu | His | Lys | Ile | Leu | Glu | Met | Glu | Gly | Lys | His | |
| 190 | | | | | 195 | | | | | 200 | | | | | 205 | |
| AAG | GAA | GAG | TTG | GAC | ACC | TTA | AAG | GAA | GAG | AAA | GAG | AAC | CTT | CAA | GGC | 972 |
| Lys | Glu | Glu | Leu | Asp | Thr | Leu | Lys | Glu | Glu | Lys | Glu | Asn | Leu | Gln | Gly | |
| | | | | 210 | | | | | 215 | | | | | 220 | | |
| TTG | GTT | ACT | CGT | CAA | ACA | TAT | ATA | ATC | CAG | GAG | CTG | GAA | AAG | CAA | TTA | 1020 |
| Leu | Val | Thr | Arg | Gln | Thr | Tyr | Ile | Ile | Gln | Glu | Leu | Glu | Lys | Gln | Leu | |
| | | | 225 | | | | | 230 | | | | | 235 | | | |
| AAC | AGA | GCT | ACC | ACC | AAC | AAC | AGT | GTC | CTT | CAG | AAG | CAG | CAA | CTG | GAG | 1068 |
| Asn | Arg | Ala | Thr | Thr | Asn | Asn | Ser | Val | Leu | Gln | Lys | Gln | Gln | Leu | Glu | |
| | | 240 | | | | | 245 | | | | | 250 | | | | |
| CTG | ATG | GAC | ACA | GTC | CAC | AAC | CTT | GTC | AAT | CTT | TGC | ACT | AAA | GAA | GGT | 1116 |
| Leu | Met | Asp | Thr | Val | His | Asn | Leu | Val | Asn | Leu | Cys | Thr | Lys | Glu | Gly | |
| | 255 | | | | | 260 | | | | | 265 | | | | | |
| GTT | TTA | CTA | AAG | GGA | GGA | AAA | AGA | GAG | GAA | GAG | AAA | CCA | TTT | AGA | GAC | 1164 |
| Val | Leu | Leu | Lys | Gly | Gly | Lys | Arg | Glu | Glu | Glu | Lys | Pro | Phe | Arg | Asp | |
| 270 | | | | | 275 | | | | | 280 | | | | | 285 | |
| TGT | GCA | GAT | GTA | TAT | CAA | GCT | GGT | TTT | AAT | AAA | AGT | GGA | ATC | TAC | ACT | 1212 |
| Cys | Ala | Asp | Val | Tyr | Gln | Ala | Gly | Phe | Asn | Lys | Ser | Gly | Ile | Tyr | Thr | |
| | | | | 290 | | | | | 295 | | | | | 300 | | |
| ATT | TAT | ATT | AAT | AAT | ATG | CCA | GAA | CCC | AAA | AAG | GTG | TTT | TGC | AAT | ATG | 1260 |
| Ile | Tyr | Ile | Asn | Asn | Met | Pro | Glu | Pro | Lys | Lys | Val | Phe | Cys | Asn | Met | |
| | | | | 305 | | | | | 310 | | | | | 315 | | |
| GAT | GTC | AAT | GGG | GGA | GGT | TGG | ACT | GTA | ATA | CAA | CAT | CGT | GAA | GAT | GCA | 1308 |
| Asp | Val | Asn | Gly | Gly | Gly | Trp | Thr | Val | Ile | Gln | His | Arg | Glu | Asp | Ala | |
| | | 320 | | | | | 325 | | | | | 330 | | | | |
| AGT | CTA | GAT | TTC | CAA | AGA | GGC | TGG | AAG | GAA | TAT | AAA | ATG | GGT | TTT | GGA | 1356 |
| Ser | Leu | Asp | Phe | Gln | Arg | Gly | Trp | Lys | Glu | Tyr | Lys | Met | Gly | Phe | Gly | |
| | 335 | | | | | 340 | | | | | 345 | | | | | |
| AAT | CCC | TCC | GGT | GAA | TAT | TGG | CTG | GGG | AAT | GAG | TTT | ATT | TTT | GCC | ATT | 1404 |
| Asn | Pro | Ser | Gly | Glu | Tyr | Trp | Leu | Gly | Asn | Glu | Phe | Ile | Phe | Ala | Ile | |
| 350 | | | | | 355 | | | | | 360 | | | | | 365 | |
| ACC | AGT | CAG | AGG | CAG | TAC | ATG | CTA | AGA | ATT | GAG | TTA | ATG | GAC | TGG | GAA | 1452 |
| Thr | Ser | Gln | Arg | Gln | Tyr | Met | Leu | Arg | Ile | Glu | Leu | Met | Asp | Trp | Glu | |
| | | | | 370 | | | | | 375 | | | | | 380 | | |
| GGG | AAC | CGA | GCC | TAT | TCA | CAG | TAT | GAC | AGA | TTC | CAC | ATA | GGA | AAT | GAA | 1500 |
| Gly | Asn | Arg | Ala | Tyr | Ser | Gln | Tyr | Asp | Arg | Phe | His | Ile | Gly | Asn | Glu | |
| | | | 385 | | | | | 390 | | | | | 395 | | | |
| AAG | CAA | AAC | TAT | AGG | TTG | TAT | TTA | AAA | GGT | CAC | ACT | GGG | ACA | GCA | GGA | 1548 |
| Lys | Gln | Asn | Tyr | Arg | Leu | Tyr | Leu | Lys | Gly | His | Thr | Gly | Thr | Ala | Gly | |
| | | 400 | | | | | 405 | | | | | 410 | | | | |
| AAA | CAG | AGC | AGC | CTG | ATC | TTA | CAC | GGT | GCT | GAT | TTC | AGC | ACT | AAA | GAT | 1596 |
| Lys | Gln | Ser | Ser | Leu | Ile | Leu | His | Gly | Ala | Asp | Phe | Ser | Thr | Lys | Asp | |
| | 415 | | | | | 420 | | | | | 425 | | | | | |
| GCT | GAT | AAT | GAC | AAC | TGT | ATG | TGC | AAA | TGT | GCC | CTC | ATG | TTA | ACA | GGA | 1644 |
| Ala | Asp | Asn | Asp | Asn | Cys | Met | Cys | Lys | Cys | Ala | Leu | Met | Leu | Thr | Gly | |
| 430 | | | | | 435 | | | | | 440 | | | | | 445 | |

| | | | | | | | | | | | | | | | | |
|---|---|---|---|---|---|---|---|---|---|---|---|---|---|---|---|---|
| GGA | TGG | TGG | TTT | GAT | GCT | TGT | GGC | CCC | TCC | AAT | CTA | AAT | GGA | ATG | TTC | 1692 |
| Gly | Trp | Trp | Phe | Asp<br>450 | Ala | Cys | Gly | Pro<br>455 | Ser | Asn | Leu | Asn | Gly | Met<br>460 | Phe | |
| TAT | ACT | GCG | GGA | CAA | AAC | CAT | GGA | AAA | CTG | AAT | GGG | ATA | AAG | TGG | CAC | 1740 |
| Tyr | Thr | Ala | Gly<br>465 | Gln | Asn | His | Gly | Lys<br>470 | Leu | Asn | Gly | Ile | Lys<br>475 | Trp | His | |
| TAC | TTC | AAA | GGG | CCC | AGT | TAC | TCC | TTA | CGT | TCC | ACA | ACT | ATG | ATG | ATT | 1788 |
| Tyr | Phe | Lys<br>480 | Gly | Pro | Ser | Tyr | Ser<br>485 | Leu | Arg | Ser | Thr | Thr<br>490 | Met | Met | Ile | |
| CGA | CCT | TTA | GAT | TTT | TGA | AAGCGCAATG | TCAGAAGCGA | TTATGAAAGC | | | | | | | | 1836 |
| Arg | Pro<br>495 | Leu | Asp | Phe | * | | | | | | | | | | | |

```
AACAAAGAAA TCCGGAGAAG CTGCCAGGTG AGAAACTGTT TGAAAACTTC AGAAGCAAAC    1896

AATATTGTCT CCCTTCCAGC AATAAGTGGT AGTTATGTGA AGTCACCAAG GTTCTTGACC    1956

GTGAATCTGG AGCCGTTTGA GTTCACAAGA GTCTCTACTT GGGGTGACAG TGCTCACGTG    2016

GCTCGACTAT AGAAAACTCC ACTGACTGTC GGGCTTTAAA AAGGGAAGAA ACTGCTGAGC    2076

TTGCTGTGCT TCAAACTACT ACTGGACCTT ATTTTGGAAC TATGGTAGCC AGATGATAAA    2136

TATGGTTAAT TTC                                                        2149
```

( 2 ) INFORMATION FOR SEQ ID NO:2:

( i ) SEQUENCE CHARACTERISTICS:
        ( A ) LENGTH: 498 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Thr | Val | Phe | Leu<br>5 | Ser | Phe | Ala | Phe | Leu<br>10 | Ala | Ala | Ile | Leu | Thr<br>15 | His |
| Ile | Gly | Cys | Ser<br>20 | Asn | Gln | Arg | Arg | Ser<br>25 | Pro | Glu | Asn | Ser | Gly<br>30 | Arg | Arg |
| Tyr | Asn | Arg<br>35 | Ile | Gln | His | Gly | Gln<br>40 | Cys | Ala | Tyr | Thr | Phe<br>45 | Ile | Leu | Pro |
| Glu | His<br>50 | Asp | Gly | Asn | Cys | Arg<br>55 | Glu | Ser | Thr | Thr | Asp<br>60 | Gln | Tyr | Asn | Thr |
| Asn<br>65 | Ala | Leu | Gln | Arg | Asp<br>70 | Ala | Pro | His | Val | Glu<br>75 | Pro | Asp | Phe | Ser | Ser<br>80 |
| Gln | Lys | Leu | Gln | His<br>85 | Leu | Glu | His | Val | Met<br>90 | Glu | Asn | Tyr | Thr | Gln<br>95 | Trp |
| Leu | Gln | Lys | Leu<br>100 | Glu | Asn | Tyr | Ile | Val<br>105 | Glu | Asn | Met | Lys | Ser<br>110 | Glu | Met |
| Ala | Gln | Ile<br>115 | Gln | Gln | Asn | Ala | Val<br>120 | Gln | Asn | His | Thr | Ala<br>125 | Thr | Met | Leu |
| Glu | Ile<br>130 | Gly | Thr | Ser | Leu | Leu<br>135 | Ser | Gln | Thr | Ala | Glu<br>140 | Gln | Thr | Arg | Lys |
| Leu<br>145 | Thr | Asp | Val | Glu | Thr<br>150 | Gln | Val | Leu | Asn | Gln<br>155 | Thr | Ser | Arg | Leu | Glu<br>160 |
| Ile | Gln | Leu | Leu | Glu<br>165 | Asn | Ser | Leu | Ser | Thr<br>170 | Tyr | Lys | Leu | Glu | Lys<br>175 | Gln |
| Leu | Leu | Gln | Gln<br>180 | Thr | Asn | Glu | Ile | Leu<br>185 | Lys | Ile | His | Glu | Lys<br>190 | Asn | Ser |
| Leu | Leu | Glu<br>195 | His | Lys | Ile | Leu | Glu<br>200 | Met | Glu | Gly | Lys | His<br>205 | Lys | Glu | Glu |

| Leu | Asp | Thr | Leu | Lys | Glu | Glu | Lys | Glu | Asn | Leu | Gln | Gly | Leu | Val | Thr |
| | 210 | | | | 215 | | | | | 220 | | | | | |
| Arg | Gln | Thr | Tyr | Ile | Ile | Gln | Glu | Leu | Glu | Lys | Gln | Leu | Asn | Arg | Ala |
| 225 | | | | | 230 | | | | 235 | | | | | | 240 |
| Thr | Thr | Asn | Asn | Ser | Val | Leu | Gln | Lys | Gln | Leu | Glu | Leu | Met | Asp | |
| | | | | 245 | | | | | 250 | | | | | 255 | |
| Thr | Val | His | Asn | Leu | Val | Asn | Leu | Cys | Thr | Lys | Glu | Gly | Val | Leu | Leu |
| | | | 260 | | | | | 265 | | | | | 270 | | |
| Lys | Gly | Gly | Lys | Arg | Glu | Glu | Lys | Pro | Phe | Arg | Asp | Cys | Ala | Asp | |
| | | | 275 | | | | 280 | | | | 285 | | | | |
| Val | Tyr | Gln | Ala | Gly | Phe | Asn | Lys | Ser | Gly | Ile | Tyr | Thr | Ile | Tyr | Ile |
| | | 290 | | | | 295 | | | | | 300 | | | | |
| Asn | Asn | Met | Pro | Glu | Pro | Lys | Lys | Val | Phe | Cys | Asn | Met | Asp | Val | Asn |
| 305 | | | | | 310 | | | | | 315 | | | | | 320 |
| Gly | Gly | Gly | Trp | Thr | Val | Ile | Gln | His | Arg | Glu | Asp | Ala | Ser | Leu | Asp |
| | | | | 325 | | | | | 330 | | | | | 335 | |
| Phe | Gln | Arg | Gly | Trp | Lys | Glu | Tyr | Lys | Met | Gly | Phe | Gly | Asn | Pro | Ser |
| | | | 340 | | | | | 345 | | | | | 350 | | |
| Gly | Glu | Tyr | Trp | Leu | Gly | Asn | Glu | Phe | Ile | Phe | Ala | Ile | Thr | Ser | Gln |
| | | 355 | | | | | 360 | | | | | 365 | | | |
| Arg | Gln | Tyr | Met | Leu | Arg | Ile | Glu | Leu | Met | Asp | Trp | Glu | Gly | Asn | Arg |
| | 370 | | | | | 375 | | | | | 380 | | | | |
| Ala | Tyr | Ser | Gln | Tyr | Asp | Arg | Phe | His | Ile | Gly | Asn | Glu | Lys | Gln | Asn |
| 385 | | | | | 390 | | | | | 395 | | | | | 400 |
| Tyr | Arg | Leu | Tyr | Leu | Lys | Gly | His | Thr | Gly | Thr | Ala | Gly | Lys | Gln | Ser |
| | | | | 405 | | | | | 410 | | | | | 415 | |
| Ser | Leu | Ile | Leu | His | Gly | Ala | Asp | Phe | Ser | Thr | Lys | Asp | Ala | Asp | Asn |
| | | | 420 | | | | | 425 | | | | | 430 | | |
| Asp | Asn | Cys | Met | Cys | Lys | Cys | Ala | Leu | Met | Leu | Thr | Gly | Gly | Trp | Trp |
| | | 435 | | | | | 440 | | | | | 445 | | | |
| Phe | Asp | Ala | Cys | Gly | Pro | Ser | Asn | Leu | Asn | Gly | Met | Phe | Tyr | Thr | Ala |
| | 450 | | | | | 455 | | | | | 460 | | | | |
| Gly | Gln | Asn | His | Gly | Lys | Leu | Asn | Gly | Ile | Lys | Trp | His | Tyr | Phe | Lys |
| 465 | | | | | 470 | | | | | 475 | | | | | 480 |
| Gly | Pro | Ser | Tyr | Ser | Leu | Arg | Ser | Thr | Thr | Met | Met | Ile | Arg | Pro | Leu |
| | | | | 485 | | | | | 490 | | | | | 495 | |
| Asp | Phe | | | | | | | | | | | | | | |

( 2 ) INFORMATION FOR SEQ ID NO:3:

( i ) SEQUENCE CHARACTERISTICS:
        ( A ) LENGTH: 2146 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 310..1803

( x i ) SEQUENCE DESCRIPTION: SEQ ID NO:3:

| | | | | | |
|---|---|---|---|---|---|
| CAGCTGACTC | AGGCAGGCTC | CATGCTGAAC | GGTCACACAG | AGAGGAAACA | ATAAATCTCA | 60 |
| GCTACTATGC | AATAAATATC | TCAAGTTTTA | ACGAAGAAAA | ACATCATTGC | AGTGAAATAA | 120 |
| AAAATTTTAA | AATTTTAGAA | CAAAGCTAAC | AAATGGCTAG | TTTTCTATGA | TTCTTCTTCA | 180 |
| AACGCTTTCT | TTGAGGGGGA | AAGAGTCAAA | CAAACAAGCA | GTTTTACCTG | AAATAAAGAA | 240 |

```
CTAGTTTTAG AGGTCAGAAG AAAGGAGCAA GTTTTGCGAG AGGCACGGAA GGAGTGTGCT                    300

GGCAGTACA ATG ACA GTT TTC CTT TCC TTT GCT TTC CTC GCT GCC ATT                        348
          Met Thr Val Phe Leu Ser Phe Ala Phe Leu Ala Ala Ile
           1               5                  10

CTG ACT CAC ATA GGG TGC AGC AAT CAG CGC CGA AGT CCA GAA AAC AGT                      396
Leu Thr His Ile Gly Cys Ser Asn Gln Arg Arg Ser Pro Glu Asn Ser
         15              20                  25

GGG AGA AGA TAT AAC CGG ATT CAA CAT GGG CAA TGT GCC TAC ACT TTC                      444
Gly Arg Arg Tyr Asn Arg Ile Gln His Gly Gln Cys Ala Tyr Thr Phe
 30              35                  40                      45

ATT CTT CCA GAA CAC GAT GGC AAC TGT CGT GAG AGT ACG ACA GAC CAG                      492
Ile Leu Pro Glu His Asp Gly Asn Cys Arg Glu Ser Thr Thr Asp Gln
             50                  55                      60

TAC AAC ACA AAC GCT CTG CAG AGA GAT GCT CCA CAC GTG GAA CCG GAT                      540
Tyr Asn Thr Asn Ala Leu Gln Arg Asp Ala Pro His Val Glu Pro Asp
             65                  70                  75

TTC TCT TCC CAG AAA CTT CAA CAT CTG GAA CAT GTG ATG GAA AAT TAT                      588
Phe Ser Ser Gln Lys Leu Gln His Leu Glu His Val Met Glu Asn Tyr
         80                  85                  90

ACT CAG TGG CTG CAA AAA CTT GAG AAT TAC ATT GTG GAA AAC ATG AAG                      636
Thr Gln Trp Leu Gln Lys Leu Glu Asn Tyr Ile Val Glu Asn Met Lys
         95                 100                 105

TCG GAG ATG GCC CAG ATA CAG CAG AAT GCA GTT CAG AAC CAC ACG GCT                      684
Ser Glu Met Ala Gln Ile Gln Gln Asn Ala Val Gln Asn His Thr Ala
110             115                 120                     125

ACC ATG CTG GAG ATA GGA ACC AGC CTC CTC TCT CAG ACT GCA GAG CAG                      732
Thr Met Leu Glu Ile Gly Thr Ser Leu Leu Ser Gln Thr Ala Glu Gln
                130                 135                 140

ACC AGA AAG CTG ACA GAT GTT GAG ACC CAG GTA CTA AAT CAA ACT TCT                      780
Thr Arg Lys Leu Thr Asp Val Glu Thr Gln Val Leu Asn Gln Thr Ser
            145                 150                 155

CGA CTT GAG ATA CAG CTG CTG GAG AAT TCA TTA TCC ACC TAC AAG CTA                      828
Arg Leu Glu Ile Gln Leu Leu Glu Asn Ser Leu Ser Thr Tyr Lys Leu
        160                 165                 170

GAG AAG CAA CTT CTT CAA CAG ACA AAT GAA ATC TTG AAG ATC CAT GAA                      876
Glu Lys Gln Leu Leu Gln Gln Thr Asn Glu Ile Leu Lys Ile His Glu
        175                 180                 185

AAA AAC AGT TTA TTA GAA CAT AAA ATC TTA GAA ATG GAA GGA AAA CAC                      924
Lys Asn Ser Leu Leu Glu His Lys Ile Leu Glu Met Glu Gly Lys His
190             195                 200                     205

AAG GAA GAG TTG GAC ACC TTA AAG GAA GAG AAA GAG AAC CTT CAA GGC                      972
Lys Glu Glu Leu Asp Thr Leu Lys Glu Glu Lys Glu Asn Leu Gln Gly
                210                 215                 220

TTG GTT ACT CGT CAA ACA TAT ATA ATC CAG GAG CTG GAA AAG CAA TTA                      1020
Leu Val Thr Arg Gln Thr Tyr Ile Ile Gln Glu Leu Glu Lys Gln Leu
            225                 230                 235

AAC AGA GCT ACC ACC AAC AAC AGT GTC CTT CAG AAG CAG CAA CTG GAG                      1068
Asn Arg Ala Thr Thr Asn Asn Ser Val Leu Gln Lys Gln Gln Leu Glu
        240                 245                 250

CTG ATG GAC ACA GTC CAC AAC CTT GTC AAT CTT TGC ACT AAA GAA GTT                      1116
Leu Met Asp Thr Val His Asn Leu Val Asn Leu Cys Thr Lys Glu Val
        255                 260                 265

TTA CTA AAG GGA GGA AAA AGA GAG GAA GAC AAA CCA TTT AGA GAC TGT                      1164
Leu Leu Lys Gly Gly Lys Arg Glu Glu Asp Lys Pro Phe Arg Asp Cys
270             275                 280                     285

GCA GAT GTA TAT CAA GCT GGT TTT AAT AAA AGT GGA ATC TAC ACT ATT                      1212
Ala Asp Val Tyr Gln Ala Gly Phe Asn Lys Ser Gly Ile Tyr Thr Ile
                290                 295                 300
```

| | | | | | | | | | | | | | | | | |
|---|---|---|---|---|---|---|---|---|---|---|---|---|---|---|---|---|
| TAT | ATT | AAT | AAT | ATG | CCA | GAA | CCC | AAA | AAG | GTG | TTT | TGC | AAT | ATG | GAT | 1260 |
| Tyr | Ile | Asn | Asn | Met | Pro | Glu | Pro | Lys | Lys | Val | Phe | Cys | Asn | Met | Asp | |
| | | | | 305 | | | | 310 | | | | | 315 | | | |
| GTC | AAT | GGG | GGA | GGT | TGG | ACT | GTA | ATA | CAA | CAT | CGT | GAA | GAT | GGA | AGT | 1308 |
| Val | Asn | Gly | Gly | Gly | Trp | Thr | Val | Ile | Gln | His | Arg | Glu | Asp | Gly | Ser | |
| | | 320 | | | | | 325 | | | | | 330 | | | | |
| CTA | GAT | TTC | CAA | AGA | GGC | TGG | AAG | GAA | TAT | AAA | ATG | GGT | TTT | GGA | AAT | 1356 |
| Leu | Asp | Phe | Gln | Arg | Gly | Trp | Lys | Glu | Tyr | Lys | Met | Gly | Phe | Gly | Asn | |
| | 335 | | | | | 340 | | | | | 345 | | | | | |
| CCC | TCC | GGT | GAA | TAT | TGG | CTG | GGG | AAT | GAG | TTT | ATT | TTT | GCC | ATT | ACC | 1404 |
| Pro | Ser | Gly | Glu | Tyr | Trp | Leu | Gly | Asn | Glu | Phe | Ile | Phe | Ala | Ile | Thr | |
| 350 | | | | | 355 | | | | | 360 | | | | | 365 | |
| AGT | CAG | AGG | CAG | TAC | ATG | CTA | AGA | ATT | GAG | TTA | ATG | GAC | TGG | GAA | GGG | 1452 |
| Ser | Gln | Arg | Gln | Tyr | Met | Leu | Arg | Ile | Glu | Leu | Met | Asp | Trp | Glu | Gly | |
| | | | | 370 | | | | | 375 | | | | | 380 | | |
| AAC | CGA | GCC | TAT | TCA | CAG | TAT | GAC | AGA | TTC | CAC | ATA | GGA | AAT | GAA | AAG | 1500 |
| Asn | Arg | Ala | Tyr | Ser | Gln | Tyr | Asp | Arg | Phe | His | Ile | Gly | Asn | Glu | Lys | |
| | | | 385 | | | | | 390 | | | | | 395 | | | |
| CAA | AAC | TAT | AGG | TTG | TAT | TTA | AAA | GGT | CAC | ACT | GGG | ACA | GCA | GGA | AAA | 1548 |
| Gln | Asn | Tyr | Arg | Leu | Tyr | Leu | Lys | Gly | His | Thr | Gly | Thr | Ala | Gly | Lys | |
| | | 400 | | | | | 405 | | | | | 410 | | | | |
| CAG | AGC | AGC | CTG | ATC | TTA | CAC | GGT | GCT | GAT | TTC | AGC | ACT | AAA | GAT | GCT | 1596 |
| Gln | Ser | Ser | Leu | Ile | Leu | His | Gly | Ala | Asp | Phe | Ser | Thr | Lys | Asp | Ala | |
| | 415 | | | | | 420 | | | | | 425 | | | | | |
| GAT | AAT | GAC | AAC | TGT | ATG | TGC | AAA | TGT | GCC | CTC | ATG | TTA | ACA | GGA | GGA | 1644 |
| Asp | Asn | Asp | Asn | Cys | Met | Cys | Lys | Cys | Ala | Leu | Met | Leu | Thr | Gly | Gly | |
| 430 | | | | | 435 | | | | | 440 | | | | | 445 | |
| TGG | TGG | TTT | GAT | GCT | TGT | GGC | CCC | TCC | AAT | CTA | AAT | GGA | ATG | TTC | TAT | 1692 |
| Trp | Trp | Phe | Asp | Ala | Cys | Gly | Pro | Ser | Asn | Leu | Asn | Gly | Met | Phe | Tyr | |
| | | | | 450 | | | | | 455 | | | | | 460 | | |
| ACT | GCG | GGA | CAA | AAC | CAT | GGA | AAA | CTG | AAT | GGG | ATA | AAG | TGG | CAC | TAC | 1740 |
| Thr | Ala | Gly | Gln | Asn | His | Gly | Lys | Leu | Asn | Gly | Ile | Lys | Trp | His | Tyr | |
| | | | 465 | | | | | 470 | | | | | 475 | | | |
| TTC | AAA | GGG | CCC | AGT | TAC | TCC | TTA | CGT | TCC | ACA | ACT | ATG | ATG | ATT | CGA | 1788 |
| Phe | Lys | Gly | Pro | Ser | Tyr | Ser | Leu | Arg | Ser | Thr | Thr | Met | Met | Ile | Arg | |
| | | | 480 | | | | 485 | | | | | 490 | | | | |
| CCT | TTA | GAT | TTT | TGA | AAGCGAATG | TCAGAAGCGA | TTATGAAAGC | AACAAAGAAA | | | | | | | | 1843 |
| Pro | Leu | Asp | Phe | * | | | | | | | | | | | | |
| | 495 | | | | | | | | | | | | | | | |

| | | | | |
|---|---|---|---|---|
| TCCGGAGAAG | CTGCCAGGTG | AGAAACTGTT | TGAAAACTTC | AGAAGCAAAC AATATTGTCT | 1903 |
| CCCTTCCAGC | AATAAGTGGT | AGTTATGTGA | AGTCACCAAG | GTTCTTGACC GTGAATCTGG | 1963 |
| AGCCGTTTGA | GTTCACAAGA | GTCTCTACTT | GGGGTGACAG | TGCTCACGTG GCTCGACTAT | 2023 |
| AGAAAACTCC | ACTGACTGTC | GGGCTTTAAA | AAGGGAAGAA | ACTGCTGAGC TTGCTGTGCT | 2083 |
| TCAAACTACT | ACTGGACCTT | ATTTTGGAAC | TATGGTAGCC | AGATGATAAA TATGGTTAAT | 2143 |
| TTC | | | | | 2146 |

( 2 ) INFORMATION FOR SEQ ID NO:4:

( i ) SEQUENCE CHARACTERISTICS:
        ( A ) LENGTH: 497 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Thr | Val | Phe | Leu | Ser | Phe | Ala | Phe | Leu | Ala | Ala | Ile | Leu | Thr | His |
| 1 | | | | 5 | | | | | 10 | | | | | 15 | |

| | | | | | | | | | | | | | | |
|---|---|---|---|---|---|---|---|---|---|---|---|---|---|---|
| Ile | Gly | Cys | Ser | Asn | Gln | Arg | Arg | Ser | Pro | Glu | Asn | Ser | Gly | Arg | Arg |
| | | | 20 | | | | 25 | | | | 30 | | | | |
| Tyr | Asn | Arg | Ile | Gln | His | Gly | Gln | Cys | Ala | Tyr | Thr | Phe | Ile | Leu | Pro |
| | | 35 | | | | 40 | | | | 45 | | | | | |
| Glu | His | Asp | Gly | Asn | Cys | Arg | Glu | Ser | Thr | Thr | Asp | Gln | Tyr | Asn | Thr |
| | 50 | | | | 55 | | | | | 60 | | | | | |
| Asn | Ala | Leu | Gln | Arg | Asp | Ala | Pro | His | Val | Glu | Pro | Asp | Phe | Ser | Ser |
| 65 | | | | | 70 | | | | 75 | | | | | | 80 |
| Gln | Lys | Leu | Gln | His | Leu | Glu | His | Val | Met | Glu | Asn | Tyr | Thr | Gln | Trp |
| | | | | 85 | | | | | 90 | | | | | 95 | |
| Leu | Gln | Lys | Leu | Glu | Asn | Tyr | Ile | Val | Glu | Asn | Met | Lys | Ser | Glu | Met |
| | | | 100 | | | | | 105 | | | | 110 | | | |
| Ala | Gln | Ile | Gln | Gln | Asn | Ala | Val | Gln | Asn | His | Thr | Ala | Thr | Met | Leu |
| | | 115 | | | | | 120 | | | | 125 | | | | |
| Glu | Ile | Gly | Thr | Ser | Leu | Leu | Ser | Gln | Thr | Ala | Glu | Gln | Thr | Arg | Lys |
| | 130 | | | | | 135 | | | | 140 | | | | | |
| Leu | Thr | Asp | Val | Glu | Thr | Gln | Val | Leu | Asn | Gln | Thr | Ser | Arg | Leu | Glu |
| 145 | | | | | 150 | | | | 155 | | | | | | 160 |
| Ile | Gln | Leu | Leu | Glu | Asn | Ser | Leu | Ser | Thr | Tyr | Lys | Leu | Glu | Lys | Gln |
| | | | | 165 | | | | | 170 | | | | | 175 | |
| Leu | Leu | Gln | Gln | Thr | Asn | Glu | Ile | Leu | Lys | Ile | His | Glu | Lys | Asn | Ser |
| | | | 180 | | | | | 185 | | | | | 190 | | |
| Leu | Leu | Glu | His | Lys | Ile | Leu | Glu | Met | Glu | Gly | Lys | His | Lys | Glu | Glu |
| | | | 195 | | | | | 200 | | | | 205 | | | |
| Leu | Asp | Thr | Leu | Lys | Glu | Glu | Lys | Glu | Asn | Leu | Gln | Gly | Leu | Val | Thr |
| | 210 | | | | | 215 | | | | 220 | | | | | |
| Arg | Gln | Thr | Tyr | Ile | Ile | Gln | Glu | Leu | Glu | Lys | Gln | Leu | Asn | Arg | Ala |
| 225 | | | | | 230 | | | | 235 | | | | | | 240 |
| Thr | Thr | Asn | Asn | Ser | Val | Leu | Gln | Lys | Gln | Gln | Leu | Glu | Leu | Met | Asp |
| | | | | 245 | | | | | 250 | | | | | 255 | |
| Thr | Val | His | Asn | Leu | Val | Asn | Leu | Cys | Thr | Lys | Glu | Val | Leu | Leu | Lys |
| | | | 260 | | | | | 265 | | | | | 270 | | |
| Gly | Gly | Lys | Arg | Glu | Glu | Asp | Lys | Pro | Phe | Arg | Asp | Cys | Ala | Asp | Val |
| | | 275 | | | | | 280 | | | | | 285 | | | |
| Tyr | Gln | Ala | Gly | Phe | Asn | Lys | Ser | Gly | Ile | Tyr | Thr | Ile | Tyr | Ile | Asn |
| | 290 | | | | | 295 | | | | | 300 | | | | |
| Asn | Met | Pro | Glu | Pro | Lys | Lys | Val | Phe | Cys | Asn | Met | Asp | Val | Asn | Gly |
| 305 | | | | | 310 | | | | | 315 | | | | | 320 |
| Gly | Gly | Trp | Thr | Val | Ile | Gln | His | Arg | Glu | Asp | Gly | Ser | Leu | Asp | Phe |
| | | | | 325 | | | | | 330 | | | | | 335 | |
| Gln | Arg | Gly | Trp | Lys | Glu | Tyr | Lys | Met | Gly | Phe | Gly | Asn | Pro | Ser | Gly |
| | | | 340 | | | | | 345 | | | | | 350 | | |
| Glu | Tyr | Trp | Leu | Gly | Asn | Glu | Phe | Ile | Phe | Ala | Ile | Thr | Ser | Gln | Arg |
| | | 355 | | | | | 360 | | | | | 365 | | | |
| Gln | Tyr | Met | Leu | Arg | Ile | Glu | Leu | Met | Asp | Trp | Glu | Gly | Asn | Arg | Ala |
| | 370 | | | | | 375 | | | | | 380 | | | | |
| Tyr | Ser | Gln | Tyr | Asp | Arg | Phe | His | Ile | Gly | Asn | Glu | Lys | Gln | Asn | Tyr |
| 385 | | | | | 390 | | | | | 395 | | | | | 400 |
| Arg | Leu | Tyr | Leu | Lys | Gly | His | Thr | Gly | Thr | Ala | Gly | Lys | Gln | Ser | Ser |
| | | | | 405 | | | | | 410 | | | | | 415 | |
| Leu | Ile | Leu | His | Gly | Ala | Asp | Phe | Ser | Thr | Lys | Asp | Ala | Asp | Asn | Asp |
| | | | 420 | | | | | 425 | | | | | 430 | | |
| Asn | Cys | Met | Cys | Lys | Cys | Ala | Leu | Met | Leu | Thr | Gly | Gly | Trp | Trp | Phe |
| | | | 435 | | | | 440 | | | | | 445 | | | |

```
Asp  Ala  Cys  Gly  Pro  Ser  Asn  Leu  Asn  Gly  Met  Phe  Tyr  Thr  Ala  Gly
     450                 455                      460

Gln  Asn  His  Gly  Lys  Leu  Asn  Gly  Ile  Lys  Trp  His  Tyr  Phe  Lys  Gly
465                      470                      475                      480

Pro  Ser  Tyr  Ser  Leu  Arg  Ser  Thr  Thr  Met  Met  Ile  Arg  Pro  Leu  Asp
                    485                      490                 495

Phe
```

(2) INFORMATION FOR SEQ ID NO:5:

(i) SEQUENCE CHARACTERISTICS:
        (A) LENGTH: 2282 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 357..1847

(xi) SEQUENCE DESCRIPTION: SEQ ID NO:5:

```
GAATTCCTGG  GTTGGTGTTT  ATCTCCTCCC  AGCCTTGAGG  GAGGGAACAA  CACTGTAGGA        60

TCTGGGGAGA  GAGGAACAAA  GGACCGTGAA  AGCTGCTCTG  TAAAAGCTGA  CACAGCCCTC       120

CCAAGTGAGC  AGGACTGTTC  TTCCCACTGC  AATCTGACAG  TTTACTGCAT  GCCTGGAGAG       180

AACACAGCAG  TAAAAACCAG  GTTTGCTACT  GGAAAAAGAG  GAAAGAGAAG  ACTTTCATTG       240

ACGGACCCAG  CCATGGCAGC  GTAGCAGCCC  TGCGTTTCAG  ACGGCAGCAG  CTCGGGACTC       300

TGGACGTGTG  TTTGCCCTCA  AGTTTGCTAA  GCTGCTGGTT  TATTACTGAA  GAAAGA          356

ATG  TGG  CAG  ATT  GTT  TTC  TTT  ACT  CTG  AGC  TGT  GAT  CTT  GTC  TTG  GCC   404
Met  Trp  Gln  Ile  Val  Phe  Phe  Thr  Leu  Ser  Cys  Asp  Leu  Val  Leu  Ala
 1                  5                        10                      15

GCA  GCC  TAT  AAC  AAC  TTT  CGG  AAG  AGC  ATG  GAC  AGC  ATA  GGA  AAG  AAG   452
Ala  Ala  Tyr  Asn  Asn  Phe  Arg  Lys  Ser  Met  Asp  Ser  Ile  Gly  Lys  Lys
                20                       25                      30

CAA  TAT  CAG  GTC  CAG  CAT  GGG  TCC  TGC  AGC  TAC  ACT  TTC  CTC  CTG  CCA   500
Gln  Tyr  Gln  Val  Gln  His  Gly  Ser  Cys  Ser  Tyr  Thr  Phe  Leu  Leu  Pro
         35                      40                      45

GAG  ATG  GAC  AAC  TGC  CGC  TCT  TCC  TCC  AGC  CCC  TAC  GTG  TCC  AAT  GCT   548
Glu  Met  Asp  Asn  Cys  Arg  Ser  Ser  Ser  Ser  Pro  Tyr  Val  Ser  Asn  Ala
     50                      55                      60

GTG  CAG  AGG  GAC  GCG  CCG  CTC  GAA  TAC  GAT  GAC  TCG  GTG  CAG  AGG  CTG   596
Val  Gln  Arg  Asp  Ala  Pro  Leu  Glu  Tyr  Asp  Asp  Ser  Val  Gln  Arg  Leu
65                      70                      75                      80

CAA  GTG  CTG  GAG  AAC  ATC  ATG  GAA  AAC  AAC  ACT  CAG  TGG  CTA  ATG  AAG   644
Gln  Val  Leu  Glu  Asn  Ile  Met  Glu  Asn  Asn  Thr  Gln  Trp  Leu  Met  Lys
                    85                      90                      95

CTT  GAG  AAT  TAT  ATC  CAG  GAC  AAC  ATG  AAG  AAA  GAA  ATG  GTA  GAG  ATA   692
Leu  Glu  Asn  Tyr  Ile  Gln  Asp  Asn  Met  Lys  Lys  Glu  Met  Val  Glu  Ile
               100                      105                     110

CAG  CAG  AAT  GCA  GTA  CAG  AAC  CAG  ACG  GCT  GTG  ATG  ATA  GAA  ATA  GGG   740
Gln  Gln  Asn  Ala  Val  Gln  Asn  Gln  Thr  Ala  Val  Met  Ile  Glu  Ile  Gly
          115                     120                     125

ACA  AAC  CTG  TTG  AAC  CAA  ACA  GCT  GAG  CAA  ACG  CGG  AAG  TTA  ACT  GAT   788
Thr  Asn  Leu  Leu  Asn  Gln  Thr  Ala  Glu  Gln  Thr  Arg  Lys  Leu  Thr  Asp
     130                     135                     140

GTG  GAA  GCC  CAA  GTA  TTA  AAT  CAG  ACC  ACG  AGA  CTT  GAA  CTT  CAG  CTC   836
Val  Glu  Ala  Gln  Val  Leu  Asn  Gln  Thr  Thr  Arg  Leu  Glu  Leu  Gln  Leu
145                     150                     155                     160
```

| | | | | | | | | | | | | | | | | |
|---|---|---|---|---|---|---|---|---|---|---|---|---|---|---|---|---|
| TTG | GAA | CAC | TCC | CTC | TCG | ACA | AAC | AAA | TTG | GAA | AAA | CAG | ATT | TTG | GAC | 884 |
| Leu | Glu | His | Ser | Leu | Ser | Thr | Asn | Lys | Leu | Glu | Lys | Gln | Ile | Leu | Asp | |
| | | | 165 | | | | | 170 | | | | | 175 | | | |
| CAG | ACC | AGT | GAA | ATA | AAC | AAA | TTG | CAA | GAT | AAG | AAC | AGT | TTC | CTA | GAA | 932 |
| Gln | Thr | Ser | Glu | Ile | Asn | Lys | Leu | Gln | Asp | Lys | Asn | Ser | Phe | Leu | Glu | |
| | | | 180 | | | | | 185 | | | | | 190 | | | |
| AAG | AAG | GTG | CTA | GCT | ATG | GAA | GAC | AAG | CAC | ATC | ATC | CAA | CTA | CAG | TCA | 980 |
| Lys | Lys | Val | Leu | Ala | Met | Glu | Asp | Lys | His | Ile | Ile | Gln | Leu | Gln | Ser | |
| | | 195 | | | | | 200 | | | | | 205 | | | | |
| ATA | AAA | GAA | GAG | AAA | GAT | CAG | CTA | CAG | GTG | TTA | GTA | TCC | AAG | CAA | AAT | 1028 |
| Ile | Lys | Glu | Glu | Lys | Asp | Gln | Leu | Gln | Val | Leu | Val | Ser | Lys | Gln | Asn | |
| | 210 | | | | | 215 | | | | | 220 | | | | | |
| TCC | ATC | ATT | GAA | GAA | CTA | GAA | AAA | AAA | ATA | GTG | ACT | GCC | ACG | GTG | AAT | 1076 |
| Ser | Ile | Ile | Glu | Glu | Leu | Glu | Lys | Lys | Ile | Val | Thr | Ala | Thr | Val | Asn | |
| 225 | | | | | 230 | | | | | 235 | | | | | 240 | |
| AAT | TCA | GTT | CTT | CAA | AAG | CAG | CAA | CAT | GAT | CTC | ATG | GAG | ACA | GTT | AAT | 1124 |
| Asn | Ser | Val | Leu | Gln | Lys | Gln | Gln | His | Asp | Leu | Met | Glu | Thr | Val | Asn | |
| | | | | 245 | | | | | 250 | | | | | 255 | | |
| AAC | TTA | CTG | ACT | ATG | ATG | TCC | ACA | TCA | AAC | TCA | GCT | AAG | GAC | CCC | ACT | 1172 |
| Asn | Leu | Leu | Thr | Met | Met | Ser | Thr | Ser | Asn | Ser | Ala | Lys | Asp | Pro | Thr | |
| | | | 260 | | | | | 265 | | | | | 270 | | | |
| GTT | GCT | AAA | GAA | GAA | CAA | ATC | AGC | TTC | AGA | GAC | TGT | GCT | GAA | GTA | TTC | 1220 |
| Val | Ala | Lys | Glu | Glu | Gln | Ile | Ser | Phe | Arg | Asp | Cys | Ala | Glu | Val | Phe | |
| | | 275 | | | | | 280 | | | | | 285 | | | | |
| AAA | TCA | GGA | CAC | ACC | ACA | AAT | GGC | ATC | TAC | ACG | TTA | ACA | TTC | CCT | AAT | 1268 |
| Lys | Ser | Gly | His | Thr | Thr | Asn | Gly | Ile | Tyr | Thr | Leu | Thr | Phe | Pro | Asn | |
| | 290 | | | | | 295 | | | | | 300 | | | | | |
| TCT | ACA | GAA | GAG | ATC | AAG | GCC | TAC | TGT | GAC | ATG | GAA | GCT | GGA | GGA | GGC | 1316 |
| Ser | Thr | Glu | Glu | Ile | Lys | Ala | Tyr | Cys | Asp | Met | Glu | Ala | Gly | Gly | Gly | |
| 305 | | | | | 310 | | | | | 315 | | | | | 320 | |
| GGG | TGG | ACA | ATT | ATT | CAG | CGA | CGT | GAG | GAT | GGC | AGC | GTT | GAT | TTT | CAG | 1364 |
| Gly | Trp | Thr | Ile | Ile | Gln | Arg | Arg | Glu | Asp | Gly | Ser | Val | Asp | Phe | Gln | |
| | | | | 325 | | | | | 330 | | | | | 335 | | |
| AGG | ACT | TGG | AAA | GAA | TAT | AAA | GTG | GGA | TTT | GGT | AAC | CCT | TCA | GGA | GAA | 1412 |
| Arg | Thr | Trp | Lys | Glu | Tyr | Lys | Val | Gly | Phe | Gly | Asn | Pro | Ser | Gly | Glu | |
| | | | 340 | | | | | 345 | | | | | 350 | | | |
| TAT | TGG | CTG | GGA | AAT | GAG | TTT | GTT | TCG | CAA | CTG | ACT | AAT | CAG | CAA | CGC | 1460 |
| Tyr | Trp | Leu | Gly | Asn | Glu | Phe | Val | Ser | Gln | Leu | Thr | Asn | Gln | Gln | Arg | |
| | | 355 | | | | | 360 | | | | | 365 | | | | |
| TAT | GTG | CTT | AAA | ATA | CAC | CTT | AAA | GAC | TGG | GAA | GGG | AAT | GAG | GCT | TAC | 1508 |
| Tyr | Val | Leu | Lys | Ile | His | Leu | Lys | Asp | Trp | Glu | Gly | Asn | Glu | Ala | Tyr | |
| | 370 | | | | | 375 | | | | | 380 | | | | | |
| TCA | TTG | TAT | GAA | CAT | TTC | TAT | CTC | TCA | AGT | GAA | GAA | CTC | AAT | TAT | AGG | 1556 |
| Ser | Leu | Tyr | Glu | His | Phe | Tyr | Leu | Ser | Ser | Glu | Glu | Leu | Asn | Tyr | Arg | |
| 385 | | | | | 390 | | | | | 395 | | | | | 400 | |
| ATT | CAC | CTT | AAA | GGA | CTT | ACA | GGG | ACA | GCC | GGC | AAA | ATA | AGC | AGC | ATC | 1604 |
| Ile | His | Leu | Lys | Gly | Leu | Thr | Gly | Thr | Ala | Gly | Lys | Ile | Ser | Ser | Ile | |
| | | | | 405 | | | | | 410 | | | | | 415 | | |
| AGC | CAA | CCA | GGA | AAT | GAT | TTT | AGC | ACA | AAG | GAT | GGA | GAC | AAC | GAC | AAA | 1652 |
| Ser | Gln | Pro | Gly | Asn | Asp | Phe | Ser | Thr | Lys | Asp | Gly | Asp | Asn | Asp | Lys | |
| | | | 420 | | | | | 425 | | | | | 430 | | | |
| TGT | ATT | TGC | AAA | TGT | TCA | CAA | ATG | CTA | ACA | GGA | GGC | TGG | TGG | TTT | GAT | 1700 |
| Cys | Ile | Cys | Lys | Cys | Ser | Gln | Met | Leu | Thr | Gly | Gly | Trp | Trp | Phe | Asp | |
| | | | 435 | | | | | 440 | | | | | 445 | | | |
| GCA | TGT | GGT | CCT | TCC | AAC | TTG | AAC | GGA | ATG | TAC | TAT | CCA | CAG | AGG | CAG | 1748 |
| Ala | Cys | Gly | Pro | Ser | Asn | Leu | Asn | Gly | Met | Tyr | Tyr | Pro | Gln | Arg | Gln | |
| | | 450 | | | | | 455 | | | | | 460 | | | | |
| AAC | ACA | AAT | AAG | TTC | AAC | GGC | ATT | AAA | TGG | TAC | TAC | TGG | AAA | GGC | TCA | 1796 |
| Asn | Thr | Asn | Lys | Phe | Asn | Gly | Ile | Lys | Trp | Tyr | Tyr | Trp | Lys | Gly | Ser | |
| 465 | | | | | 470 | | | | | 475 | | | | | 480 | |

```
GGC TAT TCG CTC AAG GCC ACA ACC ATG ATG ATC CGA CCA GCA GAT TTC       1844
Gly Tyr Ser Leu Lys Ala Thr Thr Met Met Ile Arg Pro Ala Asp Phe
            485                 490                 495

TAA ACATCCCAGT CCACCTGAGG AACTGTCTCG AACTATTTC  AAAGACTTAA            1897
 *

GCCCAGTGCA CTGAAAGTCA CGGCTGCGCA CTGTGTCCTC TTCCACCACA GAGGGCGTGT    1957

GCTCGGTGCT GACGGGACCC ACATGCTCCA GATTAGAGCC TGTAAACTTT ATCACTTAAA    2017

CTTGCATCAC TTAACGGACC AAAGCAAGAC CCTAAACATC CATAATTGTG ATTAGACAGA    2077

ACACCTATGC AAAGATGAAC CCGAGGCTGA GAATCAGACT GACAGTTTAC AGACGCTGCT    2137

GTCACAACCA AGAATGTTAT GTGCAAGTTT ATCAGTAAAT AACTGGAAAA CAGAACACTT    2197

ATGTTATACA ATACAGATCA TCTTGGAACT GCATTCTTCT GAGCACTGTT TATACACTGT    2257

GTAAATACCC ATATGTCCTG AATTC                                          2282
```

( 2 ) INFORMATION FOR SEQ ID NO:6:

( i ) SEQUENCE CHARACTERISTICS:
        ( A ) LENGTH: 496 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240
```

-continued

| | | | | | | | | | | | | | | | |
|---|---|---|---|---|---|---|---|---|---|---|---|---|---|---|---|
| Asn | Ser | Val | Leu | Gln<br>245 | Lys | Gln | Gln | His | Asp<br>250 | Leu | Met | Glu | Thr | Val<br>255 | Asn |
| Asn | Leu | Leu | Thr<br>260 | Met | Met | Ser | Thr | Ser<br>265 | Asn | Ser | Ala | Lys | Asp<br>270 | Pro | Thr |
| Val | Ala | Lys<br>275 | Glu | Glu | Gln | Ile | Ser<br>280 | Phe | Arg | Asp | Cys | Ala<br>285 | Glu | Val | Phe |
| Lys | Ser<br>290 | Gly | His | Thr | Thr | Asn<br>295 | Gly | Ile | Tyr | Thr | Leu<br>300 | Thr | Phe | Pro | Asn |
| Ser<br>305 | Thr | Glu | Glu | Ile | Lys<br>310 | Ala | Tyr | Cys | Asp | Met<br>315 | Glu | Ala | Gly | Gly | Gly<br>320 |
| Gly | Trp | Thr | Ile | Ile<br>325 | Gln | Arg | Arg | Glu | Asp<br>330 | Gly | Ser | Val | Asp | Phe<br>335 | Gln |
| Arg | Thr | Trp | Lys<br>340 | Glu | Tyr | Lys | Val | Gly<br>345 | Phe | Gly | Asn | Pro | Ser<br>350 | Gly | Glu |
| Tyr | Trp | Leu<br>355 | Gly | Asn | Glu | Phe | Val<br>360 | Ser | Gln | Leu | Thr | Asn<br>365 | Gln | Gln | Arg |
| Tyr | Val<br>370 | Leu | Lys | Ile | His | Leu<br>375 | Lys | Asp | Trp | Glu | Gly<br>380 | Asn | Glu | Ala | Tyr |
| Ser<br>385 | Leu | Tyr | Glu | His | Phe<br>390 | Tyr | Leu | Ser | Ser | Glu<br>395 | Glu | Leu | Asn | Tyr | Arg<br>400 |
| Ile | His | Leu | Lys | Gly<br>405 | Leu | Thr | Gly | Thr | Ala<br>410 | Gly | Lys | Ile | Ser | Ser<br>415 | Ile |
| Ser | Gln | Pro | Gly<br>420 | Asn | Asp | Phe | Ser | Thr<br>425 | Lys | Asp | Gly | Asp | Asn<br>430 | Asp | Lys |
| Cys | Ile | Cys<br>435 | Lys | Cys | Ser | Gln | Met<br>440 | Leu | Thr | Gly | Gly | Trp<br>445 | Trp | Phe | Asp |
| Ala | Cys<br>450 | Gly | Pro | Ser | Asn | Leu<br>455 | Asn | Gly | Met | Tyr | Tyr<br>460 | Pro | Gln | Arg | Gln |
| Asn<br>465 | Thr | Asn | Lys | Phe | Asn<br>470 | Gly | Ile | Lys | Trp | Tyr<br>475 | Tyr | Trp | Lys | Gly | Ser<br>480 |
| Gly | Tyr | Ser | Leu | Lys<br>485 | Ala | Thr | Thr | Met | Met<br>490 | Ile | Arg | Pro | Ala | Asp<br>495 | Phe |

What is claimed is:

1. An isolated nucleic acid molecule comprising a nucleotide sequence encoding human TIE-2 ligand-2, wherein the nucleotide sequence is selected from the group consisting of:
   (a) a nucleotide sequence encoding human TIE-2 ligand-2 as set forth in FIGS. 6A and 6B (SEQ I.D. NO. 5); and
   (b) a nucleotide sequence that, as a result of the degeneracy of the genetic code, differs from the nucleotide sequence of (a) and encodes a TIE-2 ligand that binds TIE-2 receptor.

2. A vector which comprises the nucleic acid molecule of claim 1.

3. An expression vector comprising a nucleic acid molecule of claim 1, wherein the nucleic acid molecule is operatively linked to an expression control sequence.

4. A host-vector system for the production of a human TIE-2 ligand which comprises the vector of claim 3, in a suitable host cell.

5. The host-vector system of claim 4, wherein the suitable host cell is a bacterial cell, yeast cell, insect cell, or mammalian cell.

6. The host-vector system of claim 4, wherein the suitable host cell is a mammalian cell.

7. The host-vector system of claim 6, wherein the mammalian cell is a COS-7 cell.

8. A method of producing a TIE-2 ligand which comprises growing cells of the host-vector system of claim 4, under conditions permitting production of the ligand and recovering the ligand so produced.

9. A method of producing a TIE-2 ligand which comprises growing cells of the host-vector system of claim 5, under conditions permitting production of the ligand and recovering the ligand so produced.

10. A method of producing a TIE-2 ligand which comprises growing cells of the host-vector system of claim 6, under conditions permitting production of the ligand and recovering the ligand so produced.

11. A method of producing a TIE-2 ligand which comprises growing cells of the host-vector system of claim 7, under conditions permitting production of the ligand and recovering the ligand so produced.

* * * * *

UNITED STATES PATENT AND TRADEMARK OFFICE
CERTIFICATE OF CORRECTION

PATENT NO.   : 5,814,464
DATED        : September 29, 1998
INVENTOR(S)  : Samuel Davis, Pamela F. Jones and George D. Yancopoulos It is certified that error appears in the above-identified patent and that said Letters Patent is hereby corrected as shown below:

<u>Title page,</u>
Item [73], Assignee, please add as follows:

-- [73] Assignee: Regeneron Pharmaceuticals, Inc.
            Tarrytown, New York --

Signed and Sealed this

Nineteenth Day of August, 2003

JAMES E. ROGAN
*Director of the United States Patent and Trademark Office*